United States Patent
Swanson

(10) Patent No.: US 8,241,277 B2
(45) Date of Patent: Aug. 14, 2012

(54) APPARATUS FOR SECURING AN ELECTROPHYSIOLOGY PROBE TO A CLAMP

(75) Inventor: David K. Swanson, Campbell, CA (US)

(73) Assignee: Endoscopic Technologies, Inc. (ESTECH), San Ramon, CA (US)

( * ) Notice: Subject to any disclaimer, the term of this patent is extended or adjusted under 35 U.S.C. 154(b) by 0 days.

(21) Appl. No.: 12/833,824

(22) Filed: Jul. 9, 2010

(65) Prior Publication Data

US 2010/0305567 A1    Dec. 2, 2010

Related U.S. Application Data

(63) Continuation of application No. 10/080,374, filed on Feb. 19, 2002, now Pat. No. 7,753,908.

(51) Int. Cl.
*A61B 18/12* (2006.01)
(52) U.S. Cl. ............... 606/41; 601/42; 601/52
(58) Field of Classification Search ........... 606/49–51; 248/205.3, 316.7; 281/30; 211/69.1; D19/77.83, D19/84.99
See application file for complete search history.

(56) References Cited

U.S. PATENT DOCUMENTS

| | | |
|---|---|---|
| 463,785 A | 11/1891 | Connable |
| 1,586,654 A | 6/1926 | Bierman |
| 2,743,726 A | 5/1956 | Grieshaber |
| 3,154,281 A | 10/1964 | Frank |
| 3,174,309 A | 3/1965 | Kobayashi |
| 3,316,913 A | 5/1967 | Swenson |
| 3,503,398 A | 3/1970 | Fogarty et al. |
| 3,802,437 A | 4/1974 | Kees |
| 3,831,607 A | 8/1974 | Lindemann |
| 3,920,021 A | 11/1975 | Hiltebrandt |
| 3,999,555 A | 12/1976 | Person |
| 4,120,302 A | 10/1978 | Ziegler |
| 4,201,213 A | 5/1980 | Townsend |
| 4,306,561 A | 12/1981 | de Medinaceli |

(Continued)

FOREIGN PATENT DOCUMENTS

EP    0106748 B1    2/1987

(Continued)

OTHER PUBLICATIONS

Action Re: Suspension, U.S. Appl. No. 10/080,378 (now USPN 6,926,712) (2 pages).

(Continued)

*Primary Examiner* — Aaron Roane
(74) *Attorney, Agent, or Firm* — Kilpatrick Townsend & Stockton LLP

(57) ABSTRACT

An apparatus for use with a clamp including a base member configured to be secured to the clamp and at least one energy transmission device carried by the base member. An apparatus for use with a clamp and a probe that carries at least one energy transmission device including a base member configured to be secured to the clamp and an engagement device associated with the base member and configured to engage the probe. A clamp including first and second clamp members, at least one of which is malleable, and a movement apparatus that moves at least one of the first and second clamp members relative to the other. A surgical system including a clamp with first and second clamp members and a device that removably mounts at least one electrode on at least one of the first and second clamp members.

14 Claims, 13 Drawing Sheets

U.S. PATENT DOCUMENTS

| | | | |
|---|---|---|---|
| 4,469,105 A | 9/1984 | Staver |
| 4,567,890 A | 2/1986 | Ohta |
| 4,646,747 A | 3/1987 | Lundback |
| 4,685,459 A | 8/1987 | Koch et al. |
| 4,819,633 A | 4/1989 | Bauer et al. |
| 4,821,719 A | 4/1989 | Fogarty |
| 4,834,090 A | 5/1989 | Moore |
| 4,924,864 A | 5/1990 | Danzig |
| 4,985,030 A | 1/1991 | Melzer et al. |
| 5,002,561 A | 3/1991 | Fisher |
| 5,100,388 A | 3/1992 | Behl et al. |
| 5,131,379 A | 7/1992 | Sewell, Jr. |
| 5,147,357 A | 9/1992 | Rose et al. |
| 5,151,102 A | 9/1992 | Kamiyama |
| 5,190,541 A | 3/1993 | Abele et al. |
| 5,250,072 A | 10/1993 | Jain |
| 5,282,812 A | 2/1994 | Suarez |
| 5,290,286 A | 3/1994 | Parins |
| 5,300,065 A | 4/1994 | Anderson |
| 5,300,087 A | 4/1994 | Knoepfler |
| 5,318,564 A | 6/1994 | Eggers |
| 5,324,288 A | 6/1994 | Billings et al. |
| 5,370,650 A | 12/1994 | Tovey et al. |
| 5,398,683 A | 3/1995 | Edwards |
| 5,441,483 A | 8/1995 | Avitall |
| 5,443,463 A | 8/1995 | Stern et al. |
| 5,445,638 A | 8/1995 | Rydell et al. |
| 5,450,846 A | 9/1995 | Goldreyer |
| 5,476,479 A | 12/1995 | Green et al. |
| 5,484,435 A | 1/1996 | Fleenor et al. |
| 5,496,312 A | 3/1996 | Klicek |
| 5,518,164 A | 5/1996 | Hooven |
| 5,540,684 A | 7/1996 | Hassler, Jr. |
| 5,545,193 A | 8/1996 | Fleischman et al. |
| 5,546,682 A | 8/1996 | Skerry |
| 5,569,274 A | 10/1996 | Rapacki et al. |
| 5,571,121 A | 11/1996 | Heifetz |
| 5,575,810 A | 11/1996 | Swanson et al. |
| 5,582,609 A | 12/1996 | Swanson et al. |
| 5,599,350 A | 2/1997 | Schulze et al. |
| 5,624,454 A | 4/1997 | Palti |
| 5,626,607 A | 5/1997 | Malecki et al. |
| 5,637,090 A | 6/1997 | McGee |
| 5,667,517 A | 9/1997 | Hooven |
| 5,673,695 A | 10/1997 | McGee et al. |
| 5,693,051 A | 12/1997 | Schulze et al. |
| 5,707,369 A | 1/1998 | Vaitekunas et al. |
| 5,746,748 A | 5/1998 | Steinberg |
| 5,755,715 A | 5/1998 | Stern et al. |
| 5,755,760 A | 5/1998 | Maguire et al. |
| 5,766,166 A | 6/1998 | Hooven |
| 5,776,130 A | 7/1998 | Buysse et al. |
| 5,782,899 A | 7/1998 | Imran |
| 5,797,905 A | 8/1998 | Fleischman et al. |
| 5,820,095 A | 10/1998 | Stone |
| 5,824,005 A | 10/1998 | Motamedi |
| 5,833,690 A | 11/1998 | Yates et al. |
| 5,837,011 A | 11/1998 | Wong |
| 5,843,101 A | 12/1998 | Fry |
| 5,846,239 A | 12/1998 | Swanson |
| 5,868,362 A | 2/1999 | Daoud |
| 5,888,198 A | 3/1999 | Eggers |
| 5,891,095 A | 4/1999 | Eggers et al. |
| 5,891,140 A | 4/1999 | Ginn et al. |
| 5,908,420 A | 6/1999 | Parins et al. |
| 5,925,038 A | 7/1999 | Panescu et al. |
| 5,938,694 A | 8/1999 | Jaraczewski |
| 5,951,549 A | 9/1999 | Richardson et al. |
| 5,961,513 A | 10/1999 | Swanson et al. |
| 5,971,983 A | 10/1999 | Lesh |
| 5,980,519 A | 11/1999 | Hahnen et al. |
| 6,004,269 A | 12/1999 | Crowley et al. |
| 6,004,320 A | 12/1999 | Casscells et al. |
| 6,010,500 A | 1/2000 | Sherman et al. |
| 6,010,516 A | 1/2000 | Hulka |
| 6,012,457 A | 1/2000 | Lesh |
| 6,022,313 A | 2/2000 | Ginn et al. |
| 6,023,638 A | 2/2000 | Swanson |
| 6,032,674 A | 3/2000 | Eggers et al. |
| 6,039,748 A | 3/2000 | Savage et al. |
| 6,050,996 A | 4/2000 | Schmaltz et al. |
| 6,056,747 A | 5/2000 | Saadat et al. |
| 6,071,279 A | 6/2000 | Whayne et al. |
| 6,076,012 A | 6/2000 | Swanson et al. |
| 6,086,586 A | 7/2000 | Hooven |
| 6,096,033 A | 8/2000 | Tu et al. |
| 6,096,037 A | 8/2000 | Mulier et al. |
| 6,113,596 A | 9/2000 | Hooven et al. |
| 6,115,626 A | 9/2000 | Whayne et al. |
| 6,139,563 A | 10/2000 | Cosgrove, III et al. |
| 6,142,994 A | 11/2000 | Swanson et al. |
| 6,152,920 A | 11/2000 | Thompson et al. |
| 6,161,543 A | 12/2000 | Cox et al. |
| 6,162,220 A | 12/2000 | Nezhat |
| 6,164,283 A | 12/2000 | Lesh |
| 6,174,309 B1 | 1/2001 | Wrublewski et al. |
| 6,179,837 B1 | 1/2001 | Hooven |
| 6,190,381 B1 | 2/2001 | Olsen et al. |
| 6,210,330 B1 | 4/2001 | Tepper |
| 6,228,104 B1 | 5/2001 | Fogarty et al. |
| 6,237,605 B1 | 5/2001 | Vaska et al. |
| 6,245,068 B1 | 6/2001 | Olson et al. |
| 6,267,761 B1 | 7/2001 | Ryan |
| 6,273,887 B1 | 8/2001 | Yamauchi et al. |
| 6,273,902 B1 | 8/2001 | Fogarty et al. |
| 6,277,117 B1 * | 8/2001 | Tetzlaff et al. .................. 606/48 |
| 6,290,699 B1 | 9/2001 | Hall et al. |
| 6,296,640 B1 | 10/2001 | Wampler et al. |
| 6,308,104 B1 | 10/2001 | Taylor et al. |
| 6,311,692 B1 | 11/2001 | Vaska et al. |
| 6,312,425 B1 | 11/2001 | Simpson et al. |
| 6,312,426 B1 | 11/2001 | Goldberg et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,330,473 B1 | 12/2001 | Swanson et al. |
| 6,334,861 B1 | 1/2002 | Chandler et al. |
| 6,350,264 B1 | 2/2002 | Hooven |
| 6,352,536 B1 | 3/2002 | Buysse et al. |
| 6,387,112 B1 | 5/2002 | Fogarty et al. |
| 6,395,325 B1 | 5/2002 | Hedge et al. |
| 6,416,508 B1 | 7/2002 | Eggers et al. |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,454,766 B1 | 9/2002 | Swanson et al. |
| 6,464,699 B1 | 10/2002 | Swanson |
| 6,464,700 B1 | 10/2002 | Koblish et al. |
| 6,468,272 B1 | 10/2002 | Koblish et al. |
| 6,471,699 B1 | 10/2002 | Fleischman et al. |
| 6,511,480 B1 | 1/2003 | Tetzlaff et al. |
| 6,514,250 B1 | 2/2003 | Jahns et al. |
| 6,517,536 B2 | 2/2003 | Hooven et al. |
| 6,522,905 B2 | 2/2003 | Desai |
| 6,522,930 B1 | 2/2003 | Schaer et al. |
| 6,529,756 B1 | 3/2003 | Phan et al. |
| 6,533,784 B2 | 3/2003 | Truckai et al. |
| 6,542,781 B1 | 4/2003 | Koblish et al. |
| 6,544,262 B2 | 4/2003 | Fleischman |
| 6,558,408 B1 | 5/2003 | Fogarty et al. |
| 6,582,429 B2 | 6/2003 | Krishnan et al. |
| 6,584,360 B2 | 6/2003 | Francischelli et al. |
| 6,595,991 B2 | 7/2003 | Tollner et al. |
| 6,610,055 B1 | 8/2003 | Swanson et al. |
| 6,645,202 B1 | 11/2003 | Pless et al. |
| 6,663,622 B1 | 12/2003 | Foley et al. |
| 6,679,882 B1 | 1/2004 | Kornerup |
| 6,685,715 B2 | 2/2004 | Danitz et al. |
| 6,692,491 B1 | 2/2004 | Phan |
| 6,692,514 B2 | 2/2004 | Fogarty et al. |
| 6,706,038 B2 | 3/2004 | Francischelli et al. |
| 6,770,071 B2 | 8/2004 | Woloszko et al. |
| 6,771,996 B2 | 8/2004 | Bowe et al. |
| 6,786,905 B2 | 9/2004 | Swanson et al. |
| 6,807,968 B2 | 10/2004 | Francischelli et al. |
| 6,837,887 B2 | 1/2005 | Woloszko et al. |
| 6,889,694 B2 | 5/2005 | Hooven |

| | | | |
|---|---|---|---|
| 6,896,673 B2 | 5/2005 | Hooven | |
| 6,899,710 B2 | 5/2005 | Hooven | |
| 6,926,712 B2 | 8/2005 | Phan | |
| 6,932,812 B2 | 8/2005 | Crowley et al. | |
| 6,932,816 B2 | 8/2005 | Phan | |
| 6,939,350 B2 | 9/2005 | Phan | |
| 6,949,098 B2 | 9/2005 | Mulier et al. | |
| 6,997,925 B2 | 2/2006 | Maguire et al. | |
| 7,020,531 B1 | 3/2006 | Colliou et al. | |
| 7,150,097 B2 | 12/2006 | Sremcich et al. | |
| 7,250,048 B2 | 7/2007 | Francischelli et al. | |
| 7,329,257 B2* | 2/2008 | Kanehira et al. | 606/52 |
| 7,753,908 B2 | 7/2010 | Swanson | |
| 2001/0025177 A1 | 9/2001 | Woloszko et al. | |
| 2002/0002372 A1 | 1/2002 | Jahns et al. | |
| 2002/0016588 A1 | 2/2002 | Wong et al. | |
| 2002/0058934 A1 | 5/2002 | Wang et al. | |
| 2002/0103484 A1 | 8/2002 | Hooven | |
| 2003/0144656 A1 | 7/2003 | Ocel | |
| 2003/0158547 A1 | 8/2003 | Phan | |
| 2003/0158548 A1 | 8/2003 | Phan et al. | |
| 2003/0158549 A1 | 8/2003 | Swanson | |
| 2004/0059324 A1 | 3/2004 | Francischelli et al. | |
| 2004/0059325 A1 | 3/2004 | Swanson | |
| 2004/0186467 A1 | 9/2004 | Swanson | |
| 2005/0019545 A1 | 1/2005 | Riebel | |
| 2005/0119648 A1 | 6/2005 | Swanson | |
| 2005/0119649 A1 | 6/2005 | Swanson | |
| 2005/0119653 A1 | 6/2005 | Swanson | |
| 2005/0119654 A1 | 6/2005 | Swanson et al. | |
| 2005/0215993 A1 | 9/2005 | Phan | |
| 2006/0155272 A1 | 7/2006 | Swanson | |
| 2006/0155274 A1 | 7/2006 | Swanson et al. | |
| 2006/0195080 A1 | 8/2006 | Ebert | |

FOREIGN PATENT DOCUMENTS

| | | |
|---|---|---|
| EP | 0484671 A2 | 5/1992 |
| EP | 0490301 A1 | 6/1992 |
| EP | 0584787 A1 | 8/1992 |
| EP | 0853922 A1 | 7/1998 |
| EP | 0856291 A1 | 8/1998 |
| EP | 1125549 A2 | 8/2001 |
| JP | 2001515751 T | 9/2001 |
| JP | 2001522622 T | 11/2001 |
| SU | 1253633 A1 | 8/1986 |
| WO | WO 99/12488 A1 | 3/1999 |
| WO | WO 00/24330 A1 | 5/2000 |
| WO | WO 00/42922 A1 | 7/2000 |
| WO | WO 01/72231 A2 | 10/2001 |
| WO | WO 01/80724 A2 | 11/2001 |
| WO | WO 03/070114 A1 | 8/2003 |

OTHER PUBLICATIONS

Advisory Action dated May 24, 2006 for U.S. Appl. No. 11/131,671, filed May 17, 2005 (3 pages).
Amendment dated Apr. 12, 2006 for U.S. Appl. No. 10/079,948 (11 pages).
Amendment dated Apr. 26, 2007 for U.S. Appl. No. 10/727,144 (13 pages).
Amendment dated Dec. 2, 2005 for U.S. Appl. No. 11/131,671, filed May 17, 2005 (14 pages).
Amendment dated Dec. 7, 2004 for U.S. Appl. No. 10/079,948 (23 pages).
Amendment dated Dec. 9, 2004 for U.S. Appl. No. 10/079,944, filed Feb. 19, 2002, now U.S. Patent No. 6,932,816 (5 pages).
Amendment dated Feb. 14, 2007 for U.S. Appl. No. 11/131,671, filed May 17, 2005 (11 pages).
Amendment dated Jan. 12, 2004 for U.S. Appl. No. 10/079,944, filed Feb. 19, 2002 (now U.S. Patent No. 6,932,816) (13 pages).
Amendment dated Jan. 15, 2004 for U.S. Appl. No. 10/079,948 (10 pages).
Amendment dated Jan. 25, 2008 for related U.S. Appl. No. 11/067,535, filed Feb. 25, 2005 (10 pages).
Amendment dated Jul. 14, 2003 for U.S. Appl. No. 10/079,944, filed Feb. 19, 2002, now U.S. Patent No. 6,932,816 (18 pages).
Amendment dated Jul. 15, 2003 for U.S. Appl. No. 10/079,948 (19 pages).
Amendment dated Jun. 26, 2008 for related U.S. Appl. No. 11/031,629, filed Jan. 8, 2005, Inventor: David K. Swanson (17 pages).
Amendment dated May 14, 2004 for U.S. Appl. No. 10/079,944, filed Feb. 19, 2002, now U.S. Patent No. 6,932,816 (12 pages).
Amendment dated May 19, 2008 for related U.S. Appl. No. 10/727,144, filed Dec. 2, 2003 (16 pages).
Amendment dated May 24, 2004 for U.S. Appl. No. 10/079,948 (20 pages).
Amendment dated May 4, 2006 for U.S. Appl. No. 11/131,671, filed May 17, 2005 (12 pages).
Amendment dated Nov. 15, 2006 for U.S. Appl. No. 10/727,144 (12 pages).
Amendment dated Oct. 17, 2005 for U.S. Appl. No. 10/079,948 (14 pages).
Amendment dated Sep. 11, 2003 for U.S. Appl. No. 10/080,378, now U.S. Patent No. 6,926,712 (10 pages).
Amendment dated Sep. 13, 2007 for U.S. Appl. No. 10/727,114 (16 pages).
Final Office Action dated Feb. 27, 2006 for U.S. Appl. No. 11/131,671, filed May 17, 2005 (10 pages).
Final Office Action dated Jul. 13, 2007 for U.S. Appl. No. 10/727,144 (9 pages).
Final Office Action dated Oct. 4, 2004 for U.S. Appl. No. 10/079,948 (15 pages).
Final Office Action dated Oct. 8, 2003 for U.S. Appl. No. 10/079,944, filed Feb. 19, 2002, now U.S Patent No. 6,932,816 (6 pages).
Final Office Action dated Oct. 8, 2003 for U.S. Appl. No. 10/079,948 (10 pages).
Interview Summary regarding Jun. 5, 2006 Interview for U.S. Appl. No. 10/079,948 (2 pages).
Interview Summary regarding May 11, 2005 Interview for U.S. Appl. No. 10/079,948 (2 pages).
Non-Final Office Action dated Apr. 2, 2003 for U.S. Appl. No. 10/080,378, now U.S. Patent No. 6,926,712 (5 pages).
Non-Final Office Action dated Aug. 25, 2006 for U.S. Appl. No. 10/727,144 (9 pages).
Non-Final Office Action dated Jan. 12, 2006 for U.S. Appl. No. 10/079,948 (13 pages).
Non-Final Office Action dated Jan. 31, 2007 for U.S. Appl. No. 10/727,144 (8 pages).
Non-Final Office Action dated Jun. 30, 2006 for U.S. Appl. No. 11/131,671, filed May 17, 2005 (12 pages).
Non-Final Office Action dated Mar. 26, 2004 for U.S. Appl. No. 10/079,948 (10 pages).
Non-Final Office Action dated Mar. 3, 2003 for U.S. Appl. No. 10/079,948 (7 pages).
Non-final Office Action dated Mar. 4, 2004 for U.S. Appl. No. 10/079,944, filed Feb. 19, 2002, now U.S. Patent No. 6,932,816, (6 pages).
Non-final Office Action dated Mar. 5, 2003 for U.S. Appl. No. 10/079,944, filed Feb. 19, 2002, now U.S. Patent No. 6,932,816 (9 pages).
Non-Final Office Action dated May 19, 2005 for U.S. Appl. No. 10/079,948 (13 pages).
Non-Final Office Action dated Oct. 4, 2004 for U.S. Appl. No. 10/079,944, filed Feb. 19, 2002, now U.S. Patent No. 6,932,816 (11 pages).
Non-Final Office Action dated Sep. 25, 2007 for U.S. Appl. No. 11/067,535, filed Feb. 25, 2005 (7 pages).
Non-Final Office Action dated Sep. 26, 2005 for U.S. Appl. No. 11/131,671, filed May 17, 2005 (9 pages).
Notice of Allowance dated Aug. 22, 2008 for U.S. Appl. No. 11/131,671, filed May 17, 2005 (6 pages).
Notice of Allowance dated Mar. 30, 2004 for U.S. Appl. No. 10/080,378 (now USPN 6,926,712) (4 pages).
Notice of Allowance dated May 10, 2007 for U.S. Appl. No. 11/131,671, filed May 17, 2005 (7 pages).
Office Action dated Jan. 18, 2008 for related U.S. Appl. No. 10/727,144, filed Dec. 2, 2003 (8 pages).
Office Action dated Jan. 30, 2008, for Japanese Patent Application No. 2003-569081, filed Nov. 25, 2002, (8 pages).

Office Action dated Mar. 26, 2008 for related U.S. Appl. No. 11/031,629, filed Jan. 8, 2005, (16 pages).
PCT International Search Report dated May 6, 2003 for PCT App. No. PCT/US02/38924.
PCT International Search Report dated Oct. 27, 2006 for PCT/US2005/045055, (5 pages).
Prosecution History for U.S. Appl. No. 10/080,378 (now USPN 6,926,712) including: Notice of Allowance dated Mar. 28, 2005 for U.S. Appl. No. 10/080,378 (now USPN 6,926,712) (6 pages).
Prosecution History for U.S. Appl. No, 10/727,114 including: Office action dated Jan. 18, 2008 for U.S. Appl. No. 10/727,114 (7 pages).
Prosecution History for U.S. Appl. No. 10/079,944, filed Feb. 19, 2002, now U.S. Patent No. 6,932,816 including: Notice of Allowance dated Jan. 18, 2005 for U.S. Appl. No. 10/079,944, filed Feb. 19, 2002, (now U.S. Patent No. 6,932,816 (6 pages).
Prosecution History for U.S. Appl. No. 10/079,948 including: Notice of Allowance dated Jun. 14, 2006 for U.S. Appl. No. 10/079,948 (6 pages).
Prosecution History for U.S. Appl. No. 11/067,535, filed Feb. 25, 2005 including: Amendment dated Jan. 25, 2008 for U.S. Appl. No. 11/067,535, filed Feb. 25, 2005 (10 pages).
Prosecution History for U.S. Appl. No. 11/131,671, filed May 17, 2005 including: Notice of Allowance dated Jan. 9, 2008 for U.S. Appl. No. 11/131,671, filed May 17, 2005 (5 pages).
Supplemental Notice of Allowability dated Apr. 6, 2004 for U.S. Appl. No. 10/080,378 (now USPN 6,926,712) (2 pages).

* cited by examiner

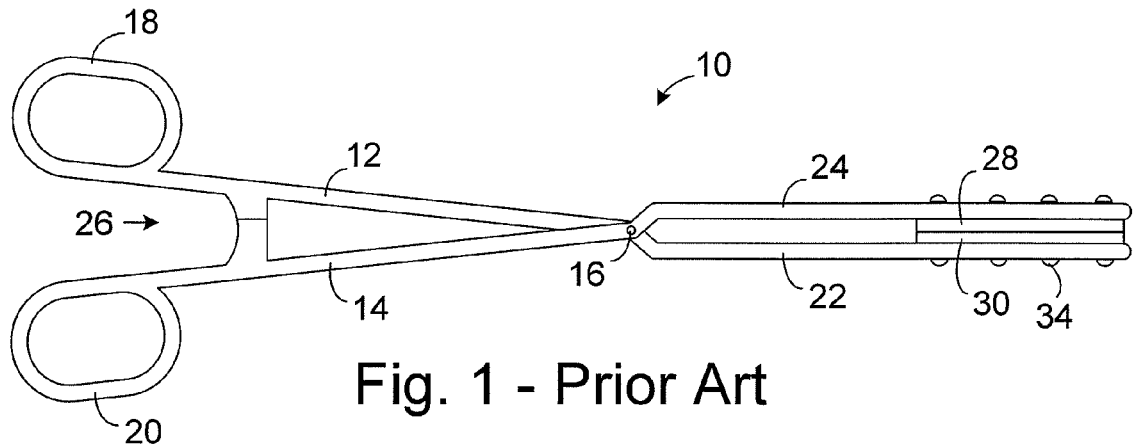
Fig. 1 - Prior Art
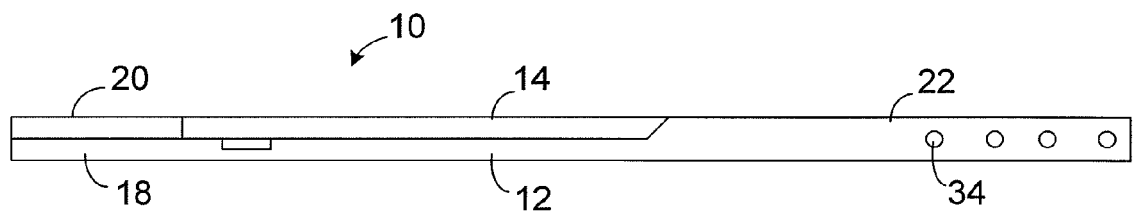
Fig. 2 - Prior Art
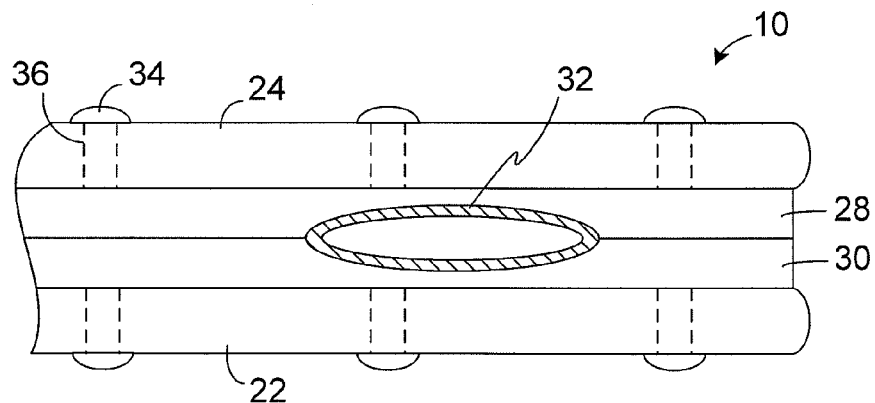
Fig. 3 - Prior Art

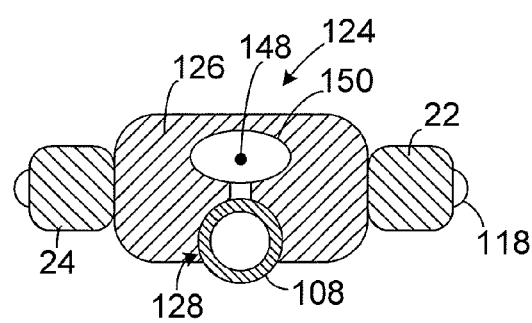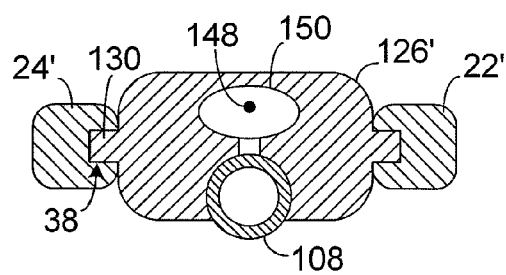
Fig. 11    Fig. 12
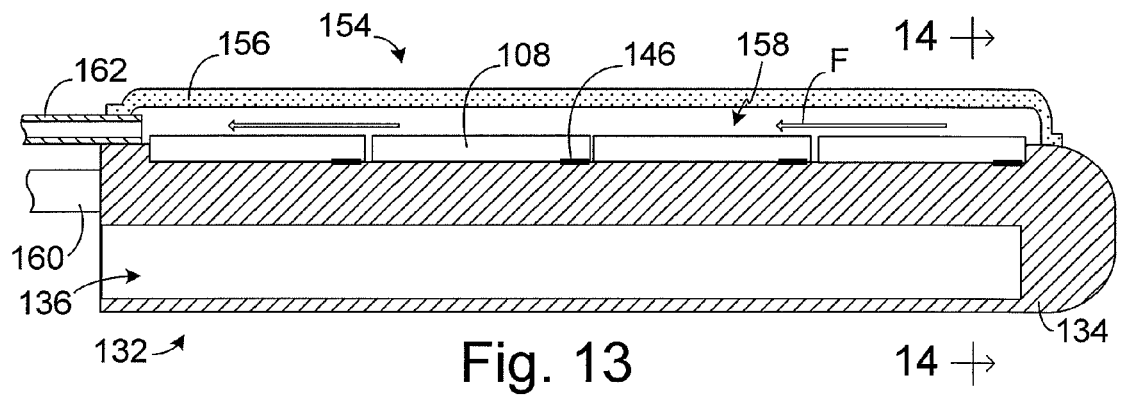
Fig. 13

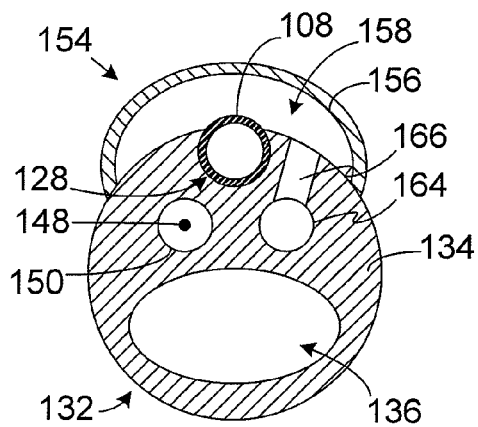
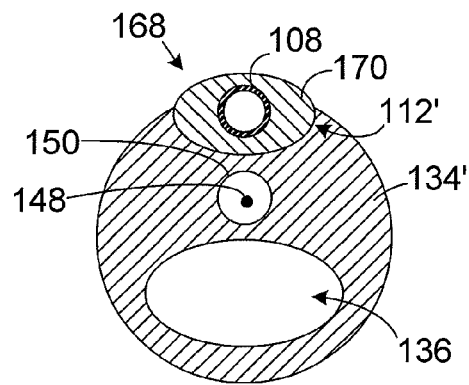
Fig. 14    Fig. 15
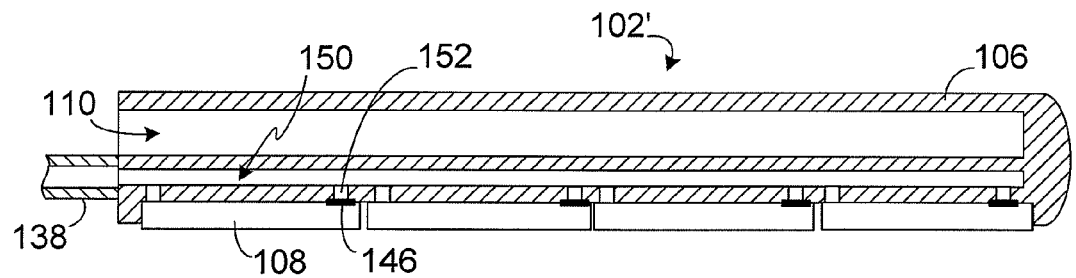
Fig. 16a
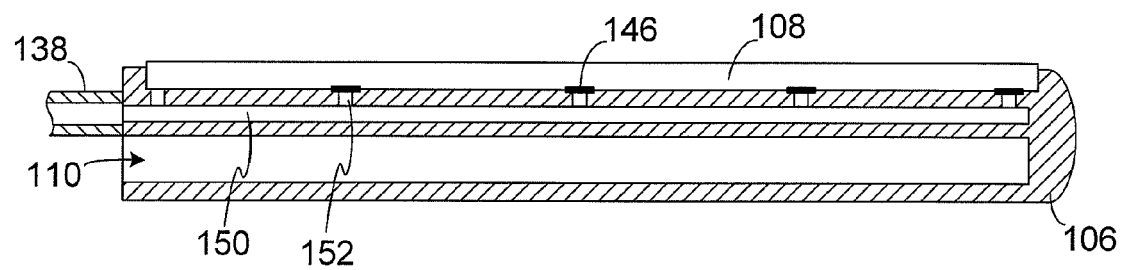
Fig. 16b

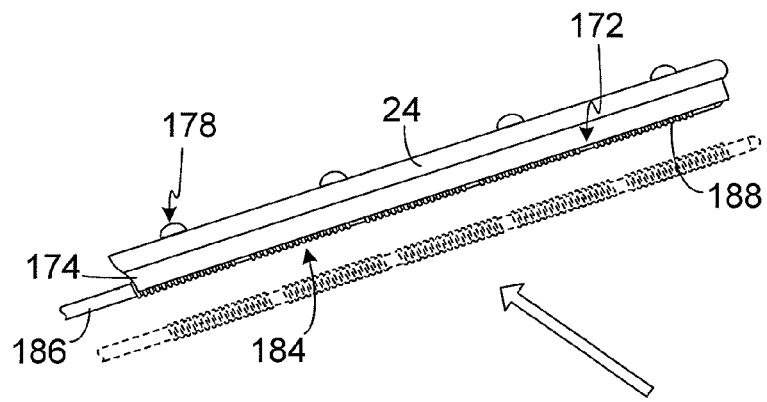
Fig. 19
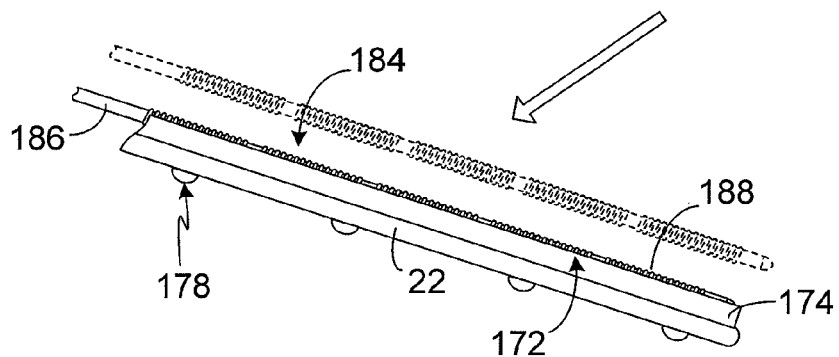
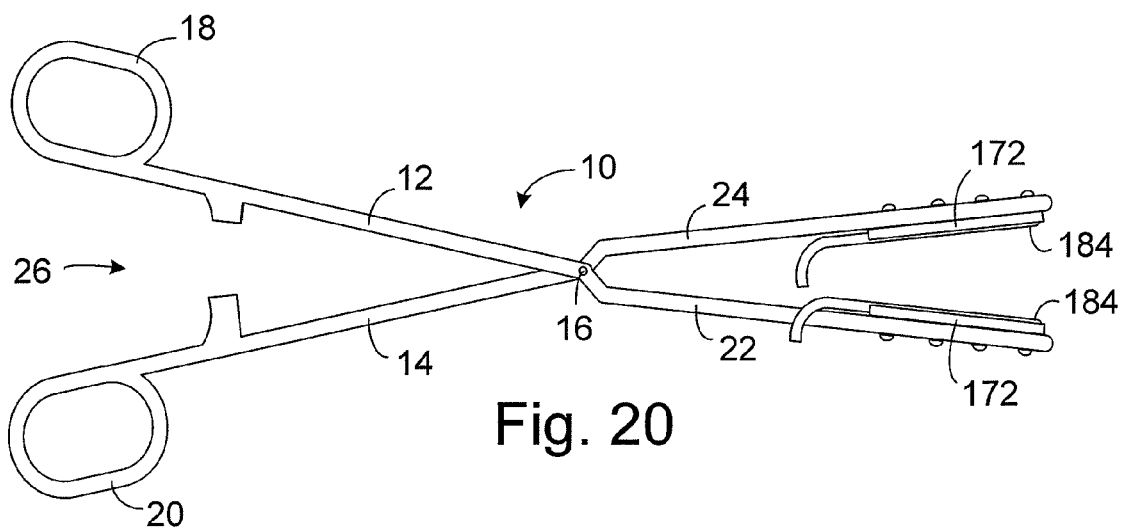
Fig. 20

APPARATUS FOR SECURING AN ELECTROPHYSIOLOGY PROBE TO A CLAMP

CROSS-REFERENCES TO RELATED APPLICATIONS

This application is a continuation of and claims the benefit of priority to U.S. patent application Ser. No. 10/080,374 filed Feb. 19, 2002 now U.S. Pat. No. 7,753,908, the contents of which are incorporated herein by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of Inventions

The present inventions relate generally to structures for positioning diagnostic and therapeutic elements within the body and, more particularly, to devices which are particularly well suited for the treatment of cardiac conditions.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery, and is very expensive. Thus, despite its considerable clinical success, only a few maze procedures are done each year.

Maze-like procedures have also been developed utilizing catheters and/or surgical probes (collectively "probes") that form lesions to create a maze for electrical conduction in a predetermined path. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions typically include a relatively long and relatively flexible body that has one or more electrodes on its distal portion. The portion of the catheter body that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter. Exemplary catheters are disclosed in U.S. Pat. No. 5,682,609.

Surgical probes used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994.

Clamps, which have a pair of opposable rigid clamp members that may be used to hold a bodily structure or a portion thereof, are used in many types surgical procedures. Lesion creating electrodes have also been permanently secured to certain types of clamps. Examples of clamps which carry lesion creating electrodes are disclosed in U.S. Pat. No. 6,142, 994. Such clamps are particularly useful when the physician intends to position electrodes on opposite sides of a body structure.

As used herein, the term "clamp" includes, but is not limited to, clamps, clips, forceps, hemostats, and any other surgical device that includes a pair of opposable clamp members that hold tissue, at least one of which is movable relative to the other. In some instances, the rigid clamp members are connected to a scissors-like arrangement including a pair of handle supporting arms that are pivotably connected to one another. The clamp members are secured to one end of the arms and the handles are secured to the other end. The clamp members come together as the handles move toward one another. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles.

The rigid clamp members in conventional clamps may be linear or have a predefined curvature that is optimized for a particular surgical procedure or portion thereof. It is, therefore, necessary to have a wide variety of clamps on hand. In the field of electrophysiology, a wide variety of clamps that have electrodes permanently secured thereto must be kept on hand.

The inventor herein has determined that it would be advantageous to provide physicians with a wide variety of devices, including clamps (both with and without energy transmission devices) and surgical probes that carry energy transmission devices, in a wide variety of shapes, and to do so in a manner that is more cost effective than conventional apparatus.

BRIEF SUMMARY OF THE INVENTION

An apparatus for use with a clamp in accordance with one embodiment of a present invention includes a base member configured to be secured to the clamp and at least one energy transmission device carried by the base member. Such an apparatus provides a number of advantages. For example, such an apparatus may be used to quickly convert a conventional clamp into an electrophysiology device. In those instances where a procedure requires a number of different clamps, the apparatus can be moved from clamp to clamp, thereby eliminating the costs associated with providing a variety of different clamps with energy transmission devices permanently secured thereto.

An apparatus for use with a clamp and a probe that carries at least one energy transmission device in accordance with one embodiment of a present invention includes a base member configured to be secured to the clamp and an engagement device associated with the base member and configured to engage the probe. Such an apparatus provides a number of advantages. For example, such an apparatus may be used to quickly convert a conventional clamp into an electrophysiology device and to achieve better (or merely different) tissue/energy transmission device contact than could be achieved with the probe itself. Additionally, in those instances where a procedure requires a number of different clamps, the apparatus can be moved from clamp to clamp, thereby eliminating the costs associated with providing a variety of different clamps with energy transmission devices permanently secured thereto.

A clamp in accordance with one embodiment of a present invention includes first and second clamp members, at least one of which is malleable, and a movement apparatus that moves at least one of the first and second clamp members relative to the other. Such a clamp provides a number of advantages. For example, the malleable clamp member allows physicians to readily reconfigure the clamp, thereby reducing the number of clamps that must be provide for a particular surgical procedure.

A surgical system in accordance with one embodiment of a present invention includes a clamp with first and second clamp members and a device that removably mounts at least one electrode on at least one of the first and second clamp members. Such a clamp provides a number of advantages. For example, the system may be used both as a conventional clamp and an electrophysiology device.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view of a conventional clamp.

FIG. 2 is a side view of the clamp illustrated in FIG. 1.

FIG. 3 is an enlarged view of a portion of the clamp illustrated in FIG. 1 holding a vein.

FIG. 8 is a section view taken along line 8-8 in FIG. 7a.

FIG. 11 is a section view taken along line 11-11 in FIG. 10.

FIG. 12 is a section view of an energy transmission assembly in accordance with a preferred embodiment of a present invention.

FIG. 13 is a section view of an energy transmission assembly in accordance with a preferred embodiment of a present invention.

FIG. 14 is a section view taken along line 14-14 in FIG. 13.

FIG. 15 is a section view of an energy transmission assembly in accordance with a preferred embodiment of a present invention.

FIG. 16a is a section view of an energy transmission assembly in accordance with a preferred embodiment of a present invention.

FIG. 16b is a section view of an energy transmission assembly in accordance with a preferred embodiment of a present invention.

FIG. 19 is a partial plan view showing a pair of the probe support devices illustrated in FIG. 17 supporting a pair of probes on a clamp.

FIG. 20 is a plan view showing a pair of the probe support devices illustrated in FIG. 17 supporting a pair of probes on a clamp.

DETAILED DESCRIPTION OF THE PREFERRED EMBODIMENTS

Figure 4:
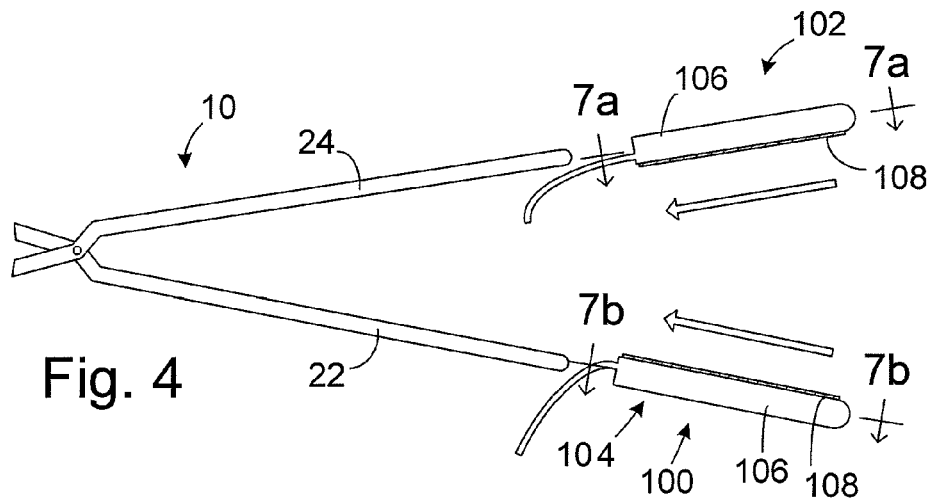
FIG. 4 is plan of a pair of energy transmission assemblies in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
I. Energy Transmission Assemblies
II. Energy Transmission Devices, Temperature Sensing and Power Control
III. Tissue Cooling Apparatus
IV. Probe Support devices
V. Clamp With Malleable Clamp Members The section titles and overall organization of the present detailed description are for the purpose of convenience only and are not intended to limit the present inventions.

This specification discloses a number of structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Energy Transmission Assemblies

Energy transmission assemblies in accordance with a present invention may be used to covert a conventional clamp into a tissue coagulation device. The energy transmission assemblies may also be used to covert a clamp in accordance with the inventions described in Section V below into a tissue coagulation device.

One example of a conventional clamp that may be used in conjunction with the present inventions is generally represented by reference numeral 10 in FIGS. 1-3. The clamp 10 includes a pair of rigid arms 12 and 14 that are pivotably connected to one another by a pin 16. The proximal ends of the arms 12 and 14 are respectively connected to a pair handle members 18 and 20, while the distal ends are respectively connected to a pair of rigid clamp members 22 and 24. A locking device 26 locks the clamp in the closed orientation, and prevents the clamp members 22 and 24 from coming any closer to one another than is illustrated in FIG. 1, thereby defining a predetermined spacing between the clamp members. The clamp 10 also includes a pair of soft, deformable inserts 28 and 30 that are removably carried by the clamp members 22 and 24. The inserts 28 and 30 allow clamp 10 to firmly grip a bodily structure 32 without damaging the bodily structure. The inserts 28 and 30 include mating structures 34 that extend through corresponding apertures 36 in the clamp members 22 and 24 to hold the inserts in place.

Figure 5:
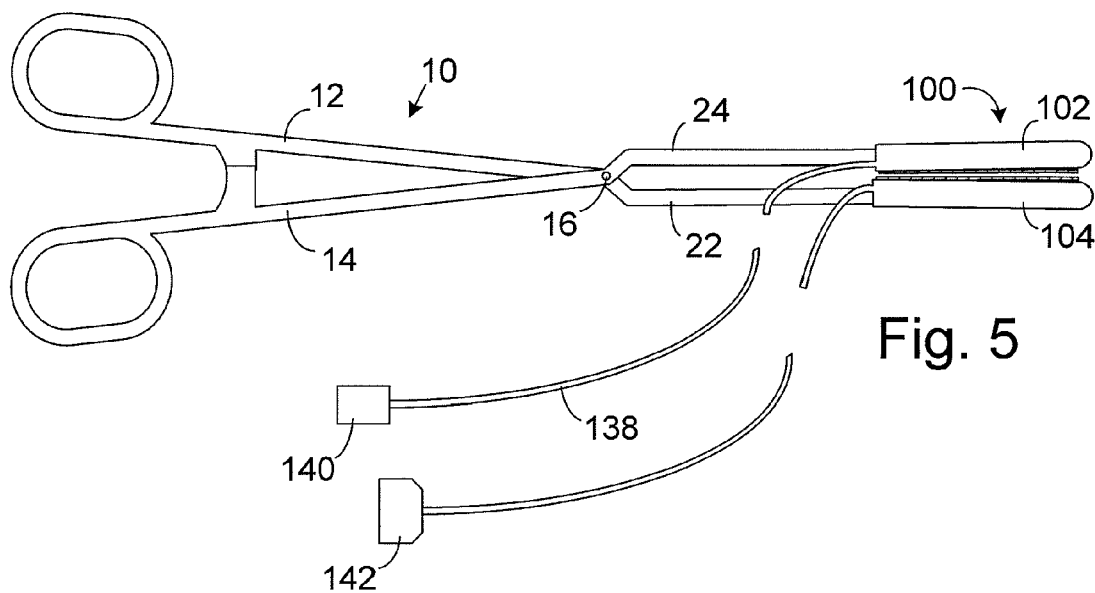
FIG. 5 is plan showing the energy transmission assemblies illustrated in FIG. 4 mounted on a clamp.

As illustrated for example in FIGS. 4 and 5, an apparatus 100 for converting the clamp 10 (which has had the inserts 28 and 30 removed) into a bi-polar tissue coagulation device includes a pair of energy transmission assemblies 102 and 104. Each of the energy transmission assemblies includes a base member 106 that may be removably secured to one of the clamp members 22 and 24 and an energy transmission device 108. [The energy transmission devices 108 are discussed in greater detail in Section II below.] Although the configuration of the energy transmission assemblies 102 and 104 may vary from application to application to suit particular situations, the energy transmission assemblies in the exemplary embodiment are configured such that they will abut one another in the same manner as the inserts 28 and 30 (FIGS. 1-3) when the clamp 10 is in the closed orientation illustrated in FIG. 5. Such an arrangement will allow the energy transmission assemblies 102 and 104 to grip a bodily structure in the same manner as the inserts 28 and 30.

Figure 7A:
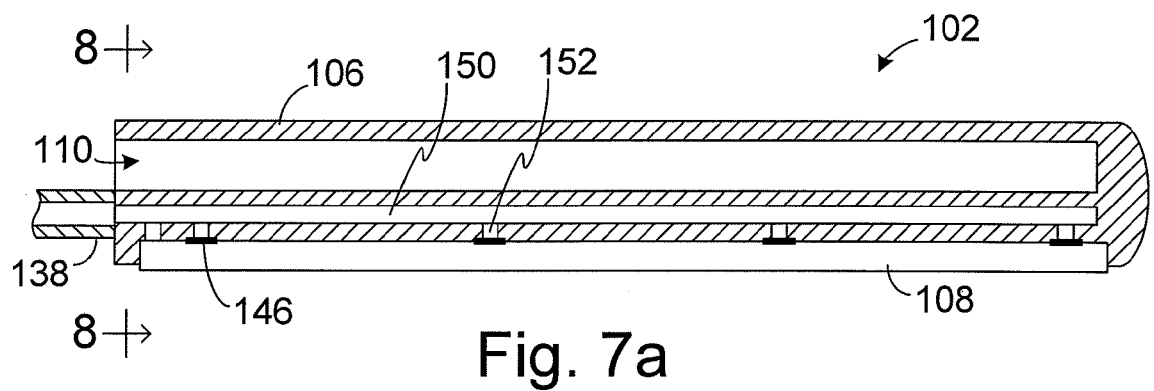
FIG. 7a is a section view taken along line 7a-7a in FIG. 4.
Figure 7B:
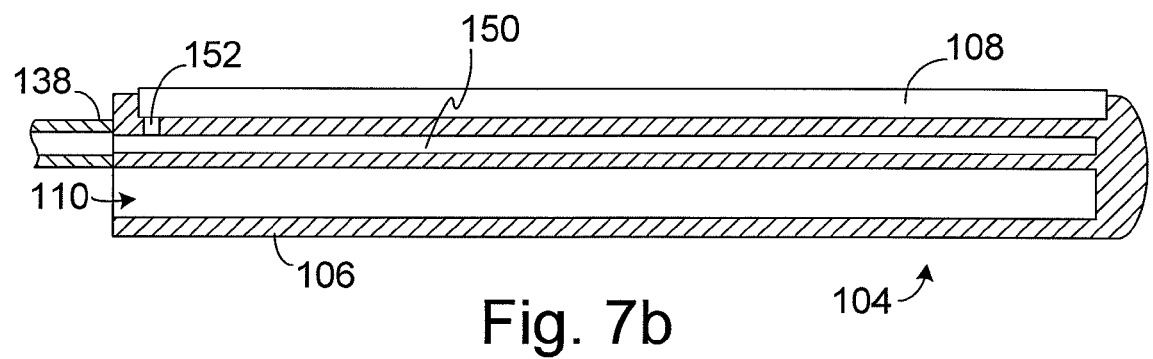
FIG. 7b is a section view taken along line 7b-7b in FIG. 4.
Figure 8:
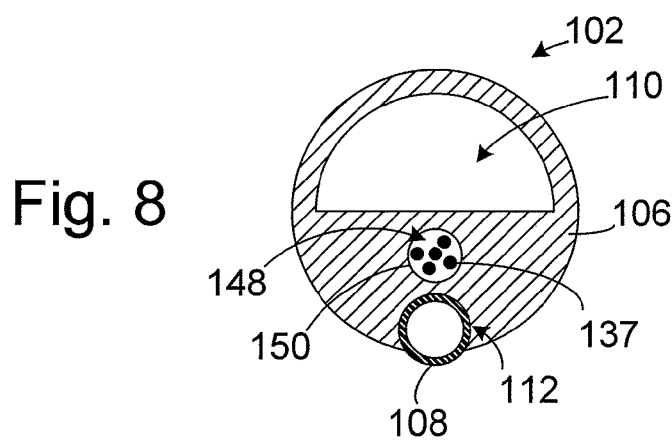

The exemplary base members 106 are preferably formed from a soft, resilient, low durometer material that is electrically insulating. Suitable materials include polyurethane, silicone and polyurethane/silicone blends having a hardness of between about 20 Shore D and about 72 Shore D. Referring to FIGS. 7a, 7b and 8, each of the exemplary base members 106 includes a longitudinally extending aperture 110 into which one of the clamp members 22 and 24 may be inserted. The apertures 110 should be sized and shaped such that the base members 106 will be forced to stretch when the clamp members 22 and 24 are inserted. If, for example, the apertures 110 have the same cross-sectional shape as the clamp members 22 and 24 (e.g. both are elliptical), then the apertures should be slightly smaller in their cross-sectional dimensions than the corresponding clamp members. The stretching of the apertures 110 creates a tight interference fit between the base members 106 and clamp members 22 and 24. Additionally, although the apertures 110 have a semi-circular cross-section in the exemplary embodiment, the apertures may have a round, rectangular, square or elliptical cross-section, or define any other cross-sectional shape, depending on the particular application.

The exemplary base members 106 also include slots 112 (FIG. 8) that secure the energy transmission devices 108 in place. The configuration of a slot 112 will, of course, depend on the configuration of the energy transmission device 108 that it is holding. The illustrated energy transmission device 108 is generally cylindrical in shape and the slot 112 has a corresponding arcuate cross-sectional shape. The arc is preferably greater than 180 degrees so that the base member 106 will deflect when the energy transmission device 108 is inserted into the slot 112 and then snap back to hold the energy transmission device in place. Adhesive may also be used to secure the energy transmission devices 108, especially in those instances where the arc is less than 180 degrees.

Figure 9A:
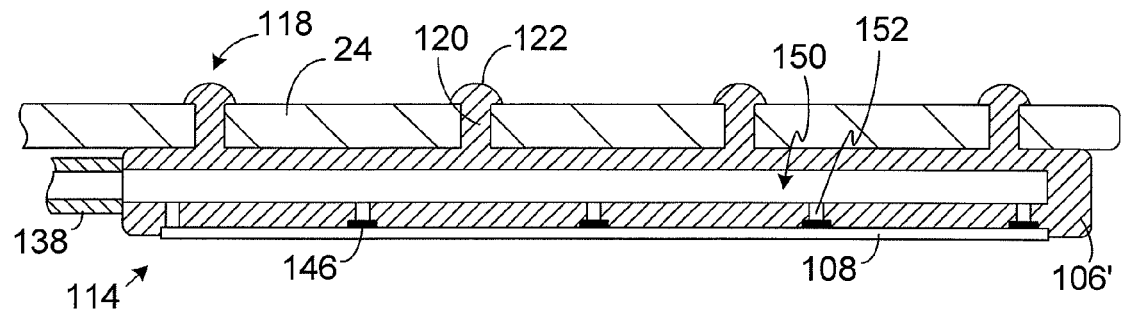
FIG. 9a is a section view of an energy transmission assembly in accordance with a preferred embodiment of a present invention.
Figure 9B:
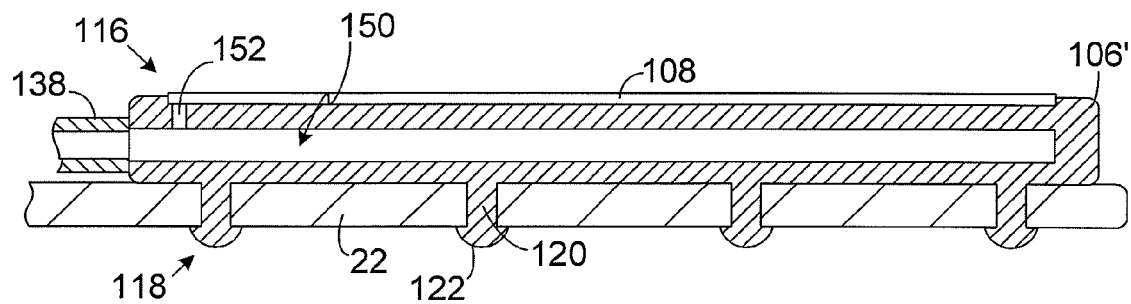
FIG. 9b is a section view of an energy transmission assembly in accordance with a preferred embodiment of a present invention.

Another exemplary apparatus for converting the clamp 10 (which has had the inserts 28 and 30 removed) into a bi-polar tissue coagulation device is illustrated in FIGS. 9a and 9b. The apparatus includes a pair of energy transmission assemblies 114 and 116 which are substantially similar to the energy transmission assemblies 102 and 104 and similar elements are represented by similar reference numerals. Each of the energy transmission assemblies 114 and 116 includes a base member 106 that may be removably secured to one of the clamp members 22 and 24 and an energy transmission device 108. Here, however, the base members 106' are secured to the clamp members 22 and 24 with mating structures 118 that mechanically engage the clamp members.

The exemplary mating structures 118, which are preferably integral with the base members 106' and formed from the same resilient material, include a relatively narrow portion 120 and a relatively wide portion 122. The relatively narrow portions are approximately the same size as the clamp member apertures 36 and the relatively wide portions 122 are slightly larger than the clamp member apertures. A removable connection is made by urging the mating structures 118 into one end of the apertures 36, thereby deforming the relatively wide portions 122, and then urging the base members 106' against the clamp members 22 and 24 until the relatively wide portions exit through the other end of the apertures and reassume their original shape.

The exemplary mating structures 118 may also be reconfigured by eliminating the relatively wide portions 122 and enlarging the relatively narrow portions 120 such that the relatively narrow portions will create an interference fit within the clamp member apertures 36. Alternatively, as discussed below with reference to FIG. 12, longitudinally extending mating structures, which also create an interference fit, may be employed when longitudinally extending slots are formed in the clamp members. Another alternative is to provide the clamp members with one or more small mating structures that extend outwardly therefrom. The clamp member mating structures will be received within apertures or slots formed in the base member.

Figure 10:
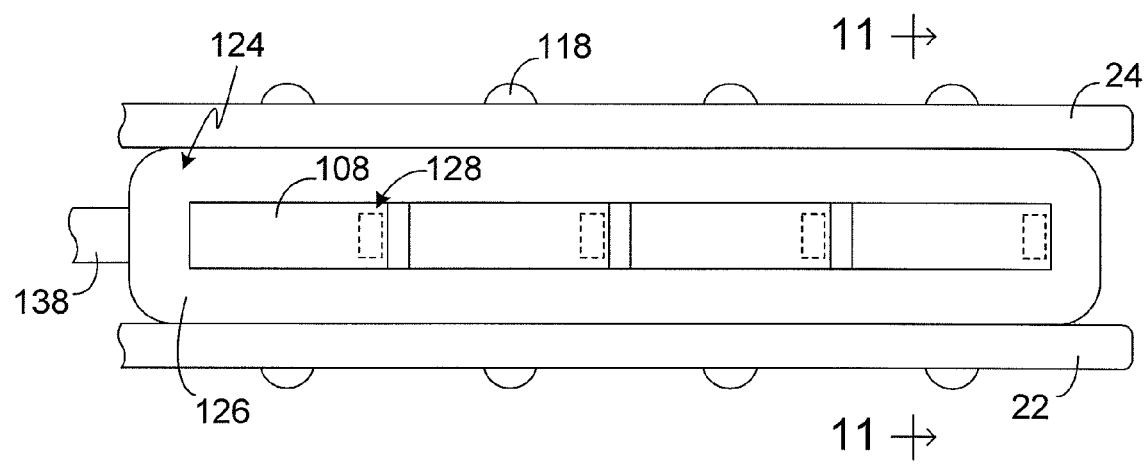
FIG. 10 is a plan view of an energy transmission assembly in accordance with a preferred embodiment of a present invention.

Turning to FIGS. 10 and 11, an energy transmission assembly 124 may be used to convert the clamp 10 (which has had the inserts 28 and 30 removed) into a uni-polar tissue coagulation device. The energy transmission assembly 124 includes a base member 126, which may be removably secured to both of the clamp members 22 and 24, and a plurality of spaced energy transmission devices 108. Although the configuration of the energy transmission assembly 124 may vary from application to application to suit particular situations, the energy transmission assembly in the exemplary embodiment is configured such that it will abut each of the clamp members when the clamp 10 is in the closed orientation illustrated in FIG. 10.

The exemplary base member 126 is preferably formed from a soft, resilient, low durometer material that is electrically insulating. Suitable materials include polyurethane, silicone and polyurethane/silicone blends having a hardness of between about 20 Shore D and about 72 Shore D. A slot 128 secures the energy transmission devices 108 in place. Although the configuration of the slot 128 will depend on the configuration of the energy transmission devices 108, the exemplary slot has an arcuate cross-sectional shape that conforms to the shape of the exemplary cylindrical energy transmission devices. The arc is preferably greater than 180 degrees so that the base member 126 will deflect when the energy transmission devices 108 are inserted into the slot 128 and then snap back to hold the energy transmission devices in place. Adhesive may also be used to secure the energy transmission devices 108 in place, especially in those instances where the are is less than 180 degrees.

The base member 126 is removably secured to the clamp members 22 and 24 with two sets of the mating structures 118 that are described above with reference to FIGS. 9a and 9b (with or without the relatively wide portions 122). Alternatively, and as illustrated for example in FIG. 12, in those instances where the clamp members 22' and 24' include longitudinally extending slots 38 instead of the apertures 36, the energy transmission assembly 124 may be provided with longitudinally extending mating structures 130 that extend outwardly from the base member 126'. The longitudinally extending mating structures 130, which are preferably integral with the base member 126' and formed from the same resilient material, are sized and shaped to create an interference fit with the slots 38. Still another alternative is to provide the clamp members with one or more small mating structures that are received within apertures or slots formed in the base member.

Another energy transmission assembly that may be used to convert the clamp 10 into a uni-polar tissue coagulation device is generally represented by reference numeral 132 in FIGS. 13 and 14. The energy transmission assembly 132 includes a base member 134 that is preferably formed from a soft, resilient, low durometer material and a plurality of energy transmission devices 108. The material which forms the base member 134 should also be electrically insulating. Suitable materials include polyurethane, silicone and polyurethane/silicone blends having a hardness of between about 20 Shore D and about 72 Shore D. A slot 128, which secures the energy transmission devices 108 in place in the manner described above with reference to FIGS. 10 and 11, is also provided.

The exemplary base member 134 includes a longitudinally extending aperture 136 into which both of the clamp members 22 and 24 may be inserted. The aperture 136 should be sized and shaped such that the base member 134 will be forced to stretch when the clamp members 22 and 24 are inserted with the clamp 10 in a closed orientation. The stretching creates a tight interference fit between the base member 134 and the clamp members 22 and 24. Additionally, although the apertures 110 have an elliptical cross-section in the exemplary embodiment, the apertures may have a round, rectangular, square or semi-circular cross-section, or define any other cross-sectional shape, depending on the particular application.

The length of the base members in the exemplary energy transmission assemblies will vary according to the intended application. In the area of cardiovascular treatments, it is anticipated that suitable lengths will range from, but are not limited to, about 2 cm to about 10 cm.

The exemplary energy transmission assemblies described above may also be modified in a variety of ways. For example, the energy transmission assembly illustrated in FIGS. 10 and 11 may be converted into a bi-polar device by simply adding a second slot 128 that is preferably spaced apart from and parallel to the existing slot. The second slot 128 could, for example, include a single return energy transmission device 108 or a plurality of spaced return energy transmission devices. Additionally, as illustrated for example in FIGS. 7a and 13, the base members and energy transmission devices in the illustrated embodiments are configured such that the energy transmission devices are generally linear and parallel to the longitudinal axis of the base members (when the assemblies are in a relaxed state and not being urged against a body structure). The base members and/or energy transmission devices may be reconfigured such that the energy transmission devices, or a portion thereof, are curved and/or non-parallel to the longitudinal axis of the base members when in the relaxed state.

II. Energy Transmission Devices, Temperature Sensing and Power Control

In the exemplary embodiments illustrated in FIGS. 4-16b, the energy transmission devices are electrodes. More specifically, the energy transmission devices are preferably in the form of wound, spiral coil electrodes that are relatively flexible. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode configuration is disclosed in U.S. Pat. No. 5,797,905. Although the diameter of the electrodes will very from application to application, the diameter preferably ranges from about 1 mm to about 3 mm for cardiovascular applications.

As an alternative, the electrodes may be in the form of solid rings of conductive material, like platinum, or can comprise a conductive material, like platinum-iridium or gold, coated upon the base member using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

When a single flexible coil electrode is carried by a base member (see, for example, FIG. 7a), the length will depend on the length of the base member and the intended application. When a plurality of spaced flexible coil electrodes are carried by a base member (see, for example, FIG. 10), the electrodes will preferably be about 10 mm to about 40 mm in length. Preferably, the electrodes will be 25 mm in length with 1 mm to 2 mm spacing, which will result in the creation of continuous lesion patterns in tissue when coagulation energy is applied simultaneously to adjacent electrodes. For rigid electrodes, the length of the each electrode can vary from about 3 mm to about 10 mm. Using multiple rigid electrodes longer than about 10 mm each adversely effects the overall flexibility of the device, while electrodes having lengths of less than about 2 mm do not consistently form the desired continuous lesion patterns.

It should also be noted that other energy transmission devices, such as laser arrays, ultrasonic transducers, microwave electrodes, and ohmically heated hot wires, may be substituted for the electrodes. Another type of energy transmission device that may be substituted for the electrodes is cryotemperature elements. Here, the energy transmission is the removal of heat from the tissue. Still another type of energy transmission device that may be substituted for the electrodes is needle projections for chemical ablation (which are preferably about 1 to 2 mm in length). Here, the energy transmission is the transmission of chemical energy.

Referring for example to FIGS. 5-8, each energy transmission device 108 is individually coupled to a wire 137 (FIG. 8) that conducts coagulating energy. The wires 137 pass in conventional fashion through cables 138 to an associated connector (140 or 142). The connectors 140 and 142 are configured to plug into an electrosurgical unit ("ESU") 144 that supplies and controls power, such RF power. A suitable ESU is the Model 4810 ESU sold by EP Technologies, Inc. of San Jose, Calif. The exemplary ESU 144 illustrated in FIG. 6 includes a plurality of displays and buttons that are used to control the level of power supplied to the energy transmission device(s) 108 and the temperature at the energy transmission device(s). When a plurality of spaced energy transmission devices 108 are employed, the ESU 144 may also be used to selectively control which of the energy transmission devices receive power. The amount of power required to coagulate tissue ranges from 5 to 150 w.

Figure 6:
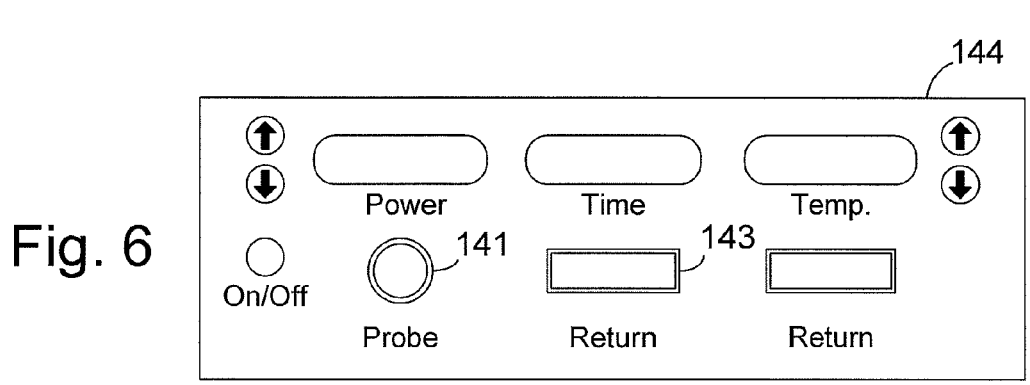
FIG. 6 is a front view of an electrosurgical unit.

The exemplary ESU 144 illustrated in FIG. 6 is operable in a bi-polar mode, where tissue coagulation energy emitted by the energy transmission device(s) 108 on one energy transmission assembly is returned through the energy transmission device(s) on another energy transmission assembly, and a uni-polar mode, where the tissue coagulation energy emitted by the energy transmission device(s) on an energy transmission assembly is returned through one or more indifferent electrodes (not shown) that are externally attached to the skin of the patient with a patch or one or more electrodes (not shown) that are positioned in the blood pool. To that end, the exemplary ESU 144 is provided with a power output connector 141 and a pair of return connectors 143. In a preferred implementation, the ESU output and return connectors 141 and 143 have different shapes to avoid confusion and the connectors 140 and 142 have corresponding shapes. As such, in the exemplary bi-polar arrangement illustrated in FIG. 5, the connector 140 associated with energy transmission assembly 102 has a shape corresponding to the ESU output connector 141 and the connector 142 associated with energy transmission assembly 104 has a shape corresponding to the ESU return connector 143.

The connector (not shown) associated with the energy transmission assembly 124 illustrated in FIG. 10, which is intended to be operated in the uni-polar mode, would have a shape corresponding to the ESU output connector 141. In those instances where it is desirable to clamp the indifferent electrode within the patient, as opposed to positioning the indifferent electrode on the patient's skin, a second energy transmission assembly may be provided with a connector having a shape corresponding to the ESU return connector 143. Additionally, in those instances where the energy transmission assembly 124 has been modified to include space electrodes (or spaced groups of longitudinally spaced electrodes) that operated in bi-polar fashion, the assembly would be provided with a pair of connectors. One would have a shape corresponding to the ESU output connector 141 and the other would have a shape corresponding to the ESU return connector 143.

With respect to power and temperature control, one or more temperature sensors 146, such as thermocouples or thermistors, may be located on, under, abutting the longitudinal end edges of, or in between, the energy transmission devices 108. A reference thermocouple (not shown) may also be provided. For temperature control purposes, signals from the temperature sensors 146 are transmitted to the ESU 144 by way of wires 148 (FIG. 8) that are connected to the connector 140 and, in some instances, the connector 142. The wires 137 and 148 (which are not shown in all of the Figures for clarity purposes) run through wire apertures 150 and small holes 152, which are formed in the base members 106, 126, 126', 134 and 134'. Suitable temperature sensors and power control schemes that are based on a sensed temperature are disclosed in U.S. Pat. Nos. 5,456,682, 5,582,609 and 5,755,715.

The actual number of temperature sensors 146 may be varied in order to suit particular applications. In the bi-polar arrangement illustrated in FIGS. 7a and 7b, for example, both of the energy transmission assemblies 102 and 104 include a single energy transmission device 108 and the energy transmission assembly 102 includes a plurality of spaced temperature sensors 146. Here, the level of power supplied to the energy transmission device 108 on the energy transmission assembly 102 would be controlled based on the highest temperature measured by the temperature sensors 146. Alternatively, the energy transmission assembly 104 (which is being used as the return) may also provided with a plurality of spaced temperature sensors 146. Here, the level of power supplied to the energy transmission device 108 on the energy transmission assembly 102 would be controlled based on the highest temperature measured by any of the temperature sensors 146, whether on the transmitting assembly 102 or the return assembly 104.

In those instances where a plurality of spaced energy transmission devices 108 are provided, such as in the uni-polar arrangement illustrated in FIG. 13, a temperature sensor 146 may be associated with each of the energy transmission devices. Here, power to the energy transmission devices 108 may be individually controlled based on the temperature measured by the associated temperature sensor 146.

Another exemplary bi-polar arrangement, which is illustrated in FIGS. 16a and 16b, is substantially similar to the arrangement illustrated in FIGS. 7a and 7b and similar reference numerals are used to represent similar elements. Here, however, the energy transmission assembly 102' includes a plurality of spaced energy transmission device 108, each having a temperature sensor 146 associated therewith, and the energy transmission assembly 104' includes a single energy transmission device 108 and a plurality of temperature sensors 146. The temperature sensors 146 are preferably positioned such that, when in use, the temperature sensors on the energy transmission assembly 102' will be aligned with the temperature sensors on the energy transmission assembly 104'. Such an arrangement allows power to the energy transmission devices 108 on the assembly 102' to be individually controlled based on the highest of two temperatures, i.e. the temperature measured by the temperature sensor 146 associated with the particular energy transmission device and the temperature measured by the temperature sensor directly across from the particular energy transmission device.

III. Tissue Cooling Apparatus

Energy transmission devices in accordance with the present inventions may also include apparatus that cools the tissue during tissue coagulation procedures. Examples of suitable cooling apparatus are illustrated in FIGS. 13-15. Such tissue cooling apparatus may also be used in conjunction with the exemplary devices illustrated in FIGS. 4, 5, 7a-12, 16a and 16b. The tissue cooling apparatus disclosed herein employ conductive fluid to cool tissue during coagulation procedures. More specifically, and as described below and in U.S. application Ser. No. 09/761,981 (which is incorporated herein by reference), heat from the tissue being coagulated is transferred to ionic fluid to cool the tissue while energy is transferred from an electrode or other energy transmission device to the tissue through the fluid by way of ionic transport. The conductive fluid may be pumped through the tissue cooling apparatus (FIGS. 13 and 14) or the tissue cooling apparatus may be saturated with the fluid prior to use (FIG. 15). In either case, cooling tissue during a coagulation procedure facilitates the formation of lesions that are wider and deeper than those that could be realized with an otherwise identical device which lacks tissue cooling apparatus.

Deferring first to FIGS. 13 and 14, an exemplary tissue cooling apparatus 154 includes a nanoporous outer casing 156 through which ionic fluid (represented by arrows F) is transferred. The ionic fluid preferably flows from one longitudinal end of the tissue cooling apparatus 154 to the other. The outer casing 156 is secured to the base member 134 over the energy transmission devices 108 such that a fluid transmission space 158 is defined therebetween. More specifically, the proximal and distal ends of the outer casing 156 are secured to the base member 134 with anchoring devices (not shown) such as lengths of heat shrink tubing, Nitinol tubing or other mechanical devices that form an interference fit between the casing and the base member. Adhesive bonding is another method of securing the outer casing 156 to the base member 134. The fluid transmission space will typically be about 0.5 mm to about 2.0 mm high and slightly wider than the associated energy transmission device(s) 108.

The ionic fluid is supplied under pressure from a fluid source (not shown) by way of a supply line 160 and is returned to the source by way of a return line 162. The supply line 160 is connected to a fluid lumen 164 that runs from the proximal end of the base member 134 to the distal region of the outer casing 156. The fluid lumen 164 is connected to the fluid transmission space 158 by an aperture 166.

The electrically conductive ionic fluid preferably possesses a low resistivity to decrease ohmic loses, and thus ohmic heating effects, within the outer casing 156. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution.

With respect to temperature and flow rate, a suitable inlet temperature for epicardial applications (the temperature will, of course, rise as heat is transferred to the fluid) is about 0 to 25° C. with a constant flow rate of about 2 to 20 ml/min. The flow rate required for endocardial applications where blood is present would be about three-fold higher (i.e. 6 to 60 ml/min.). Should applications so require, a flow rate of up to 100 ml/min. may be employed. In a closed system where the fluid is stored in a flexible bag, such as the Viaflex® bag manufactured by Baxter Corporation, and heated fluid is returned to the bag, it has been found that a volume of fluid between about 200 and 500 ml within the bag will remain at room temperature (about 22° C.) when the flow rate is between about 2 ml/min. and 20 ml/min. Alternatively, in an open system, the flexible bag should include enough fluid to complete the procedure. 160 ml would, for example, be required for a 20 minute procedure where the flow rate was 8 ml/min.

The fluid pressure within the outer casing 156 should be about 30 mm Hg in order to provide a structure that will resiliently conform to the tissue surface in response to a relatively small force normal to the tissue. Pressures above about 100 mm Hg will cause the outer casing 156 to become too stiff to properly conform to the tissue surface. For that reason, the flow resistance to and from the outer casing 156 should be relatively low.

The pores in the nanoporous outer casing 156 allow the transport of ions contained in the fluid through the casing and into contact with tissue. Thus, when an energy transmission device 108 transmit RF energy into the ionic fluid, the ionic fluid establishes an electrically conductive path through the outer casing 156 to the tissue being coagulated. Regenerated cellulose membrane materials, typically used for blood oxygenation, dialysis or ultrafiltration, are a suitable nanoporous material for the outer casing 156. The thickness of the material should be about 0.002 to 0.005 inch. Although regenerated cellulose is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within the outer casing 156.

Hydro-Fluoro™ material, which is disclosed in U.S. application Ser. No. 09/573,071, filed May 16, 2000,.is another material that may be used. Materials such as nylons (with a softening temperature above 100° C.), PTFE, PEI and PEEK that have nanopores created through the use of lasers, electrostatic discharge, ion beam bombardment or other processes may also be used. Such materials would preferably include a hydrophilic coating. Nanoporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur.

The electrical resistivity of the outer casing 156 will have a significant influence on lesion geometry and controllability. Low-resistivity (below about 500 ohm-cm) requires more RF power and results in deeper lesions, while high-resistivity (at or above about 500 ohm-cm) generates more uniform heating and improves controllability. Because of the additional heat generated by the increased body resistivity, less RF power is required to reach similar tissue temperatures after the same interval of time. Consequently, lesions generated with high-resistivity structures usually have smaller depth. The electrical resistivity of the outer casing can be controlled by specifying the pore size of the material, the porosity of the material, and the water adsorption characteristics (hydrophilic versus hydrophobic) of the material. A detailed discussion of these characteristics is found in U.S. Pat. No. 5,961,513. A suitable electrical resistivity for epicardial and endocardial lesion formation is about 1 to 3000 ohm-cm measured wet.

Generally speaking, low or essentially no liquid perfusion through the nanoporous outer casing 156 is preferred. When undisturbed by attendant liquid perfusion, ionic transport creates a continuous virtual electrode at the tissue interface. The virtual electrode efficiently transfers RF energy without need for an electrically conductive metal surface.

Pore diameters smaller than about 0.1 µm retain macromolecules, but allow ionic transfer through the pores in response to the applied RF field. With smaller pore diameters, pressure driven liquid perfusion through the pores is less likely to accompany the ionic transport, unless relatively high pressure conditions develop within the outer casing 156. Larger pore diameters (up to 8 µm) can also be used to permit ionic current flow across the membrane in response to the applied RF field. With larger pore diameters, pressure driven fluid transport across the membrane is much higher and macromolecules (such as protein) and even small blood cells (such as platelets) could cross the membrane and contaminate the inside of the probe. Red blood cells would normally not cross the membrane barrier, even if fluid perfusion across the membrane stops. On balance, a pore diameter of 1 to 5 ||m is suitable for epicardial and endocardial lesion formation. Where a larger pore diameter is employed, thereby resulting in significant fluid transfer through the porous region, a saline solution having a sodium chloride concentration of about 0.9% weight by volume would be preferred.

With respect to porosity, which represents the volumetric percentage of the outer casing 156 that is composed of pores and not occupied by the casing material, the magnitude of the porosity affects electrical resistance. Low-porosity materials have high electrical resistivity, whereas high-porosity materials have low electrical resistivity. The porosity of the outer casing 156 should be at least 1% for epicardial and endocardial applications employing a 1 to 5 µm pore diameter.

Turning to water absorption characteristics, hydrophilic materials are generally preferable because they possess a greater capacity to provide ionic transfer of RF energy without significant liquid flow through the material.

The exemplary tissue cooling apparatus 168 illustrated in FIG. 15 consists of a wettable fluid retention element 170 that is simply saturated with ionic fluid (such as saline) prior to use, as opposed to having the fluid pumped through the apparatus in the manner described above with reference to FIGS. 13 and 14. The energy transmission device(s) 108 are carried within the fluid retention element 170. Suitable materials for the fluid retention element 170 include biocompatible fabrics commonly used for vascular patches (such as woven Dacron®) open cell foam materials, hydrogels, nanoporous balloon materials (with very slow fluid delivery to the surface), and hydrophilic nanoporous materials. The effective electrical resistivity of the fluid retention element 170 when wetted with 0.9% saline (normal saline) should range from about 1 Ω-cm to about 2000 Ω-cm. A preferred resistivity for epicardial and endocardial procedures is about 1000 Ω-cm.

IV. Probe Support Devices

Probe support devices in accordance with a present invention may be used to covert a conventional clamp, or a clamp in accordance with the inventions described in Section V below, into a tissue coagulation device by securing one or more conventional catheters, surgical probes, or other apparatus that support energy transmission devices, to the clamp. Although the configuration of the probe support devices may vary from application to application to suit particular situations, the exemplary probe support devices are configured such that the probes being supported will abut one another in the same manner as the inserts 28 and 30 (FIGS. 1-3) when the associated clamp is in the closed orientation. Such an arrangement will allow the energy transmission devices on the probes to face one another in the manner similar to that described in Section I above.

Figure 17:
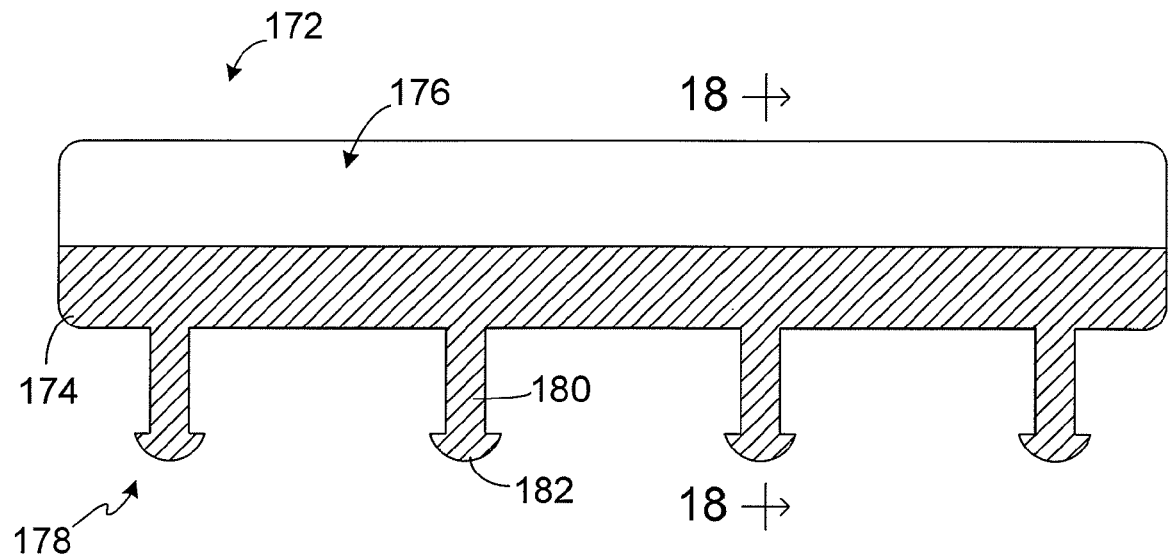
FIG. 17 is a section view of a probe support device in accordance with a preferred embodiment of a present invention.
Figure 18:
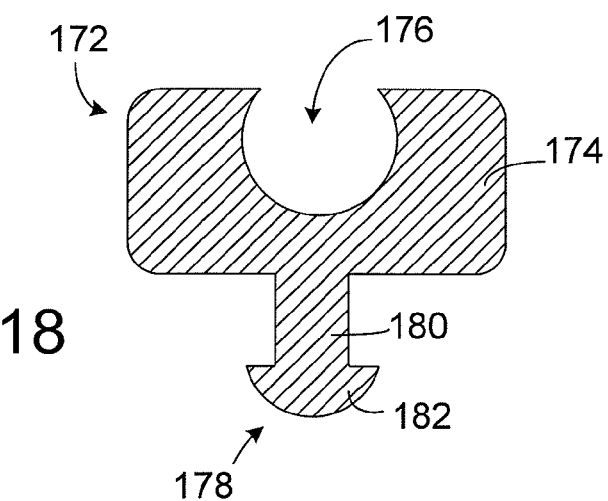
FIG. 18 is a section view taken along line 18-18 in FIG. 17.
Figure 21:
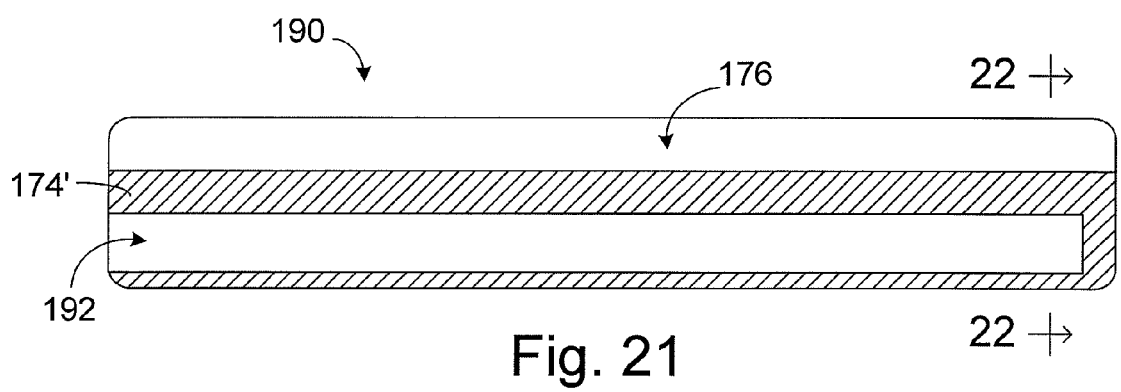
FIG. 21 is a section view of a probe support device in accordance with a preferred embodiment of a present invention.
Figure 22:
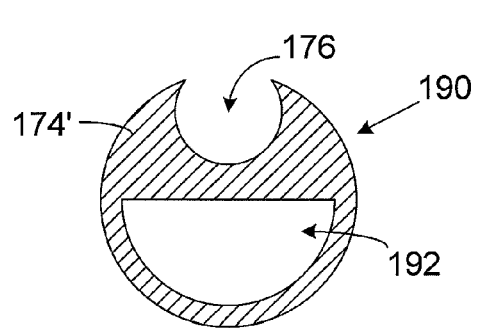
FIG. 22 is a section view taken along line 21-21 in FIG. 20.

As illustrated for example in FIGS. 17 and 18, a probe support device 172 in accordance with one embodiment of a present invention includes a base member 174, a slot 176 configured to receive an electrode supporting device such as a catheter or surgical probe, and a plurality of mating structures 178 that mechanically engage a clamp member. The exemplary base member 174 is preferably formed from a soft, resilient, low durometer material that is electrically insulating. Suitable materials include polyurethane, silicone and illustrated in FIGS. 17 and 18 and similar structural element are represented by similar reference numerals. The exemplary probe support device 190 may also be used in the manner described above with reference to FIGS. 19 and 20. Here, however, the mating structures 178 have been eliminated and the base member 172 is provided with a longitudinally extending aperture 192 into which one of the clamp members 22 and 24 may be inserted.

The aperture 192 should be sized and shaped such that the base member 174' will be forced to stretch when one of the clamp members 22 and 24 is inserted. If, for example, the apertures 192 have the same cross-sectional shape as the clamp members 22 and 24 (e.g. both are elliptical), then the apertures should be slightly smaller in their cross-sectional dimensions than the corresponding clamp members. The stretching of base member 174' creates a tight interference fit between the base member and the clamp member. Additionally, although the aperture 192 has a semi-circular cross-section in the exemplary embodiment, the apertures may have a round, rectangular, square or elliptical cross-section, or define any other cross-sectional shape, depending on the particular application.

Figure 23:
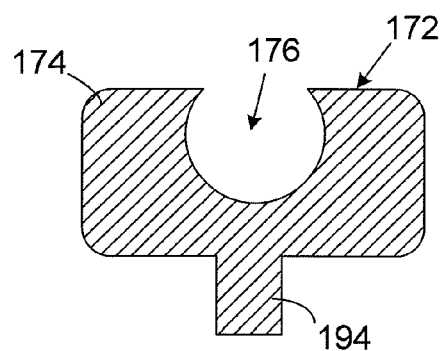
FIG. 23 is a section view of a probe support device in accordance with a preferred embodiment of a present invention.

Alternatively, and as illustrated for example in FIG. 23, in those instances where the clamp members include longitudinally extending slots instead of apertures (such as the slots 38 described above with reference to FIG. 12), the probe support device 172 may be provided with a longitudinally extending mating structure 194 that extends outwardly from the base member 174. The longitudinally extending mating structure 194, which is preferably integral with the base member 174 and formed from the same resilient material, is sized to create an interference fit with a slot. Still another alternative is to provide the clamp members with one or more small mating structures that are received within apertures or slots formed in the base member 174.

Figure 24:
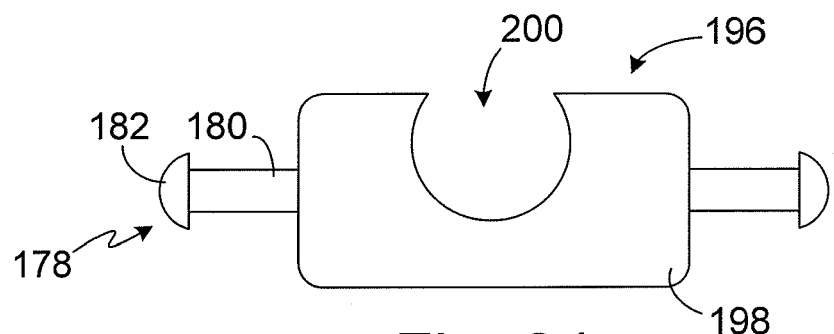
FIG. 24 is an end view of a probe support device in accordance with a preferred embodiment of a present invention.
Figure 25:
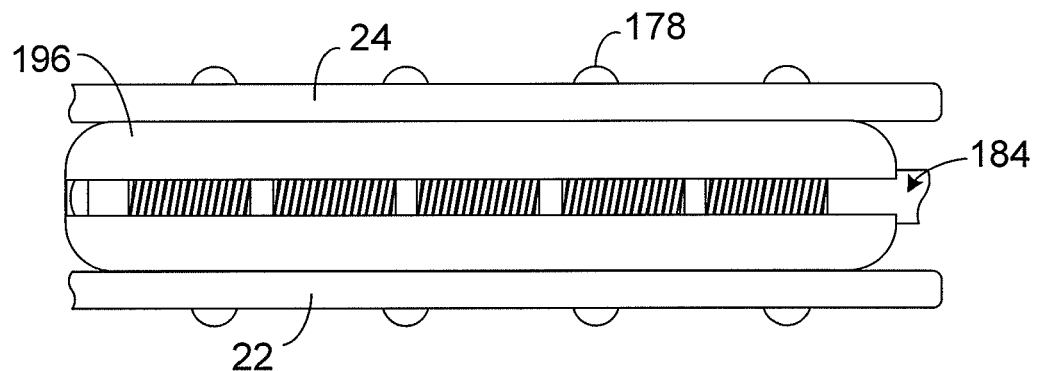
FIG. 25 is a plan view of a probe support device illustrated in FIG. 24.

An exemplary probe support device 196 that may be used in conjunction with a probe 184 to convert the clamp 10 (which has had the inserts 28 and 30 removed) into a uni-polar tissue coagulation device is illustrated in FIGS. 24 and 25. Although the configuration of the probe support device 196 may vary from application to application to suit particular situations, the probe support device in the exemplary embodiment is configured such that it will abut each of the clamp members 22 and 24 when the clamp is in the closed orientation illustrated in FIG. 25.

The exemplary probe support device 196 includes a base member 198, a slot 200 configured to receive a probe 184 or other electrode supporting device, and a plurality of mating structures 178 that mechanically engage a clamp members 22 and 24 in the manner described above. The exemplary base member 198 is preferably formed from a soft, resilient, low durometer material that is electrically insulating. Suitable materials include polyurethane, silicone and polyurethane/silicone blends having a hardness of between about 20 Shore D and about 72 Shore D. The size and shape of the slot 200 will depend on the size and shape of the probe that it is intended to hold. The exemplary probe 184 is generally cylindrical in shape and, according, the exemplary slot 200 has a corresponding arcuate cross-sectional shape. The arc is preferably greater than 180 degrees so that the base member 198 will deflect when the probe 184 is inserted into the slot 200 and then snap back to hold the probe in place.

Figure 26:
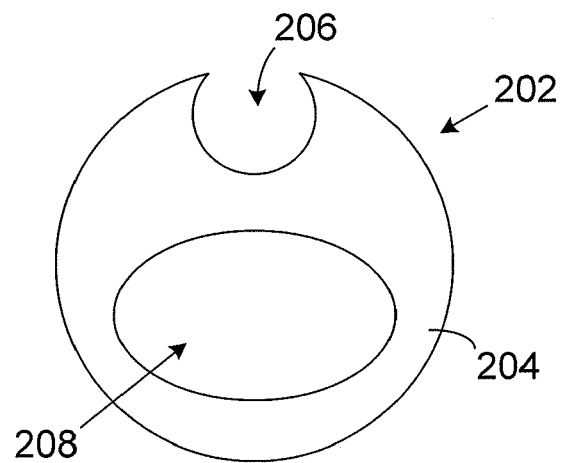
FIG. 26 is an end view of a probe support device in accordance with a preferred embodiment of a present invention.

Another exemplary probe support device that may be used in conjunction with a probe 184 to convert the clamp 10 into a uni-polar tissue coagulation device is generally represented by reference numeral 202 in FIG. 26, The probe support device 202 includes a base member 204, a slot 206 configured to receive a probe 184 or other electrode supporting device, and a longitudinally extending aperture 208 into which both of the clamp members 22 and 24 may be inserted. The exemplary base member 204 is preferably formed from a soft, resilient, low durometer material that is electrically insulating. Suitable materials include polyurethane, silicone and polyurethane/silicone blends having a hardness of between about 20 Shore D and about 72 Shore D. The size and shape of the slot 206 will depend on the size and shape of the probe that it is intended to hold, as is described above with reference to slot 200. The aperture 208 should be sized and shaped such that the base member 204 will be forced to stretch when the clamp members 22 and 24 are inserted with the clamp 10 in a closed orientation. The stretching creates a tight interference fit between the base member 204 and the clamp members 22 and 24. Additionally, although the aperture 208 has an elliptical cross-section in the exemplary embodiment, the aperture may have a round, rectangular, square or semi-circular cross-section, or define any other cross-sectional shape, depending on the particular application.

The length of the base members in the exemplary probe support devices will vary according to the intended application. In the area of cardiovascular treatments, it is anticipated that suitable lengths will range from, but are not limited to, about 3 cm to about 10 cm.

V. Clamp With Malleable Clamp Members

This portion of the specification refers to rigid and malleable structures. A rigid structure is a structure than cannot be readily bent by a physician. A malleable structure can be readily bent by the physician to a desired shape, without springing back when released, so that it will remain in that shape during the surgical procedure. Thus, the stiffness of a malleable structure must be low enough to allow the structure to be bent, but high enough to resist bending when the forces associated with a surgical procedure are applied to the structure. Rigid structures are preferably formed from stainless steel, while malleable structure are preferably farmed from annealed stainless steel or titanium. Additional information concerning malleable structures may be found in U.S. Pat. No. 6,142,994,.which is incorporated herein by reference.

Figure 27:
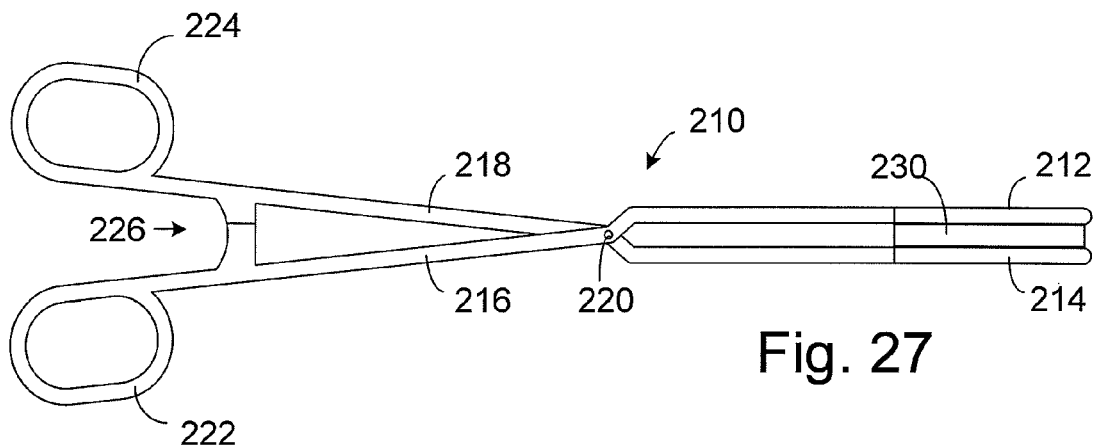
FIG. 27 is a plan view of a clamp in accordance with a preferred embodiment of a present invention.

As illustrated for example in FIG. 27, a clamp 210 in accordance with a preferred embodiment of a present invention includes a pair of malleable clamp members 212 and 214. The malleable clamp members 212 and 214 are carried at the distal ends of a pair of arms 216 and 218. The arms 216 and 218 are pivotably secured to one another by a pin 220 to allow the clamp members 212 and 214 to be moved towards and away from one another between opened and closed positions. The arms 216 and 218 are preferably formed from rigid material, but may also be malleable if desired. When rigid, the arms 216 and 218 may be linear or have a preformed curvature.

A pair of handles 222 and 224 are mounted on the proximal ends of the arms 216 and 218. A locking device 226 locks the clamp 210 in the closed orientation illustrated in FIG. 27. The locking device 226 also prevents the clamp members 212 and 214 from coming any closer to one another than is illustrated in FIG. 27, thereby defining a predetermined spacing between the clamp members.

The malleability of the clamp members 212 and 214 allows them to be re-shaped by the physician as needed for particular procedures and body structures. As such, a single clamp 210 is capable of taking the place of a number of conventional clamps with rigid clamp members. In some implementations, the clamp members 212 and 214 will be more malleable (i.e. easier to bend) at their distal end than at their proximal end. This may be accomplished by gradually decreasing the cross-sectional area of each clamp member 212 and 214 from the proximal end to the distal end.

The clamp members 212 and 214 may also be provided with holes 228 (FIG. 31) that allow soft deformable inserts, such as the conventional inserts 28 and 30 described above with reference to FIGS. 1-3. The exemplary clamp 210 may also be used in conjunction with the energy transmission assemblies, probe support devices, and probes described in Sections I-IV above.

Figure 32:
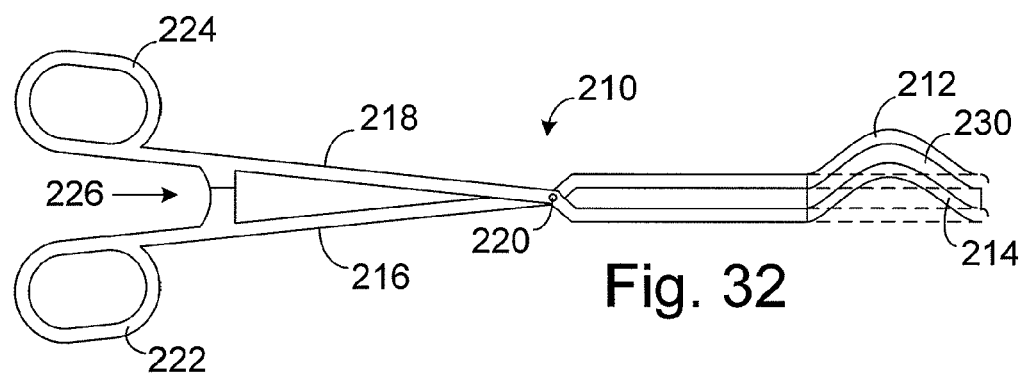
FIG. 32 is a plan view showing one example of how the clamp illustrated in FIG. 27 may be bent.

There will be many instances where it will be important to maintain the predefined spacing between the malleable clamp members 212 and 214 during the bending process in order to insure that the predefined spacing will remain when the bending process is complete. To that end, the exemplary clamp 210 is provided with a malleable insert 230 that is sized and shaped (rectangular in the exemplary implementation) to be held between the malleable clamp members 212 and 214 when the clamp is closed and locked. The friction between the clamp members 212 and 214 and insert 230 will hold the insert in place during bending. Nevertheless, if desired, the insert 230 may be provided with small protrusions that will be received by the holes 228. The malleable insert 2:30, which is preferably formed from the same material as the malleable clamp members 212 and 214, will bend with the clamp members during the bending process, thereby maintaining the predetermined spacing. [Note FIG. 32.]

Figure 28:
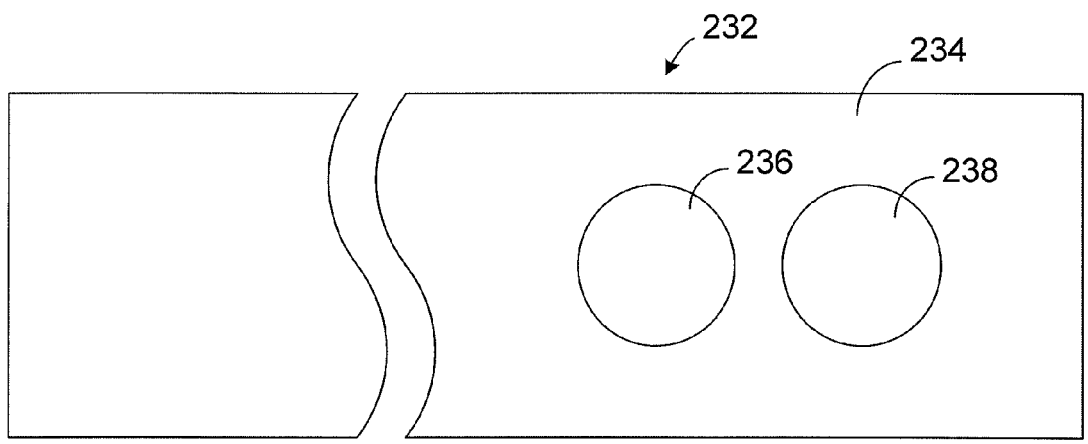
FIG. 28 is a plan view of a mandrel in accordance with a preferred embodiment of a present invention.
Figure 29:
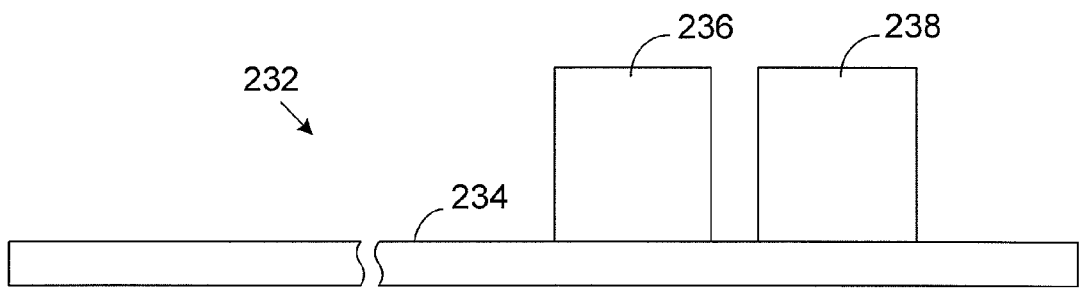
FIG. 29 is a side view of the mandrel illustrated in FIG. 28.

The exemplary mandrel 232 illustrated in FIGS. 28 and 29 may be used to bend the malleable clamp members 212 and 214. The exemplary mandrel 232 includes a base 234 and a pair of cylindrical posts 236 and 238. Posts of other shapes, such as elliptical posts, may also be employed to achieve particular bends. The mandrel 232 should also be formed from material that is harder than the malleable clamp members 212 and 214, such as stainless steel or titanium.

Figure 30:
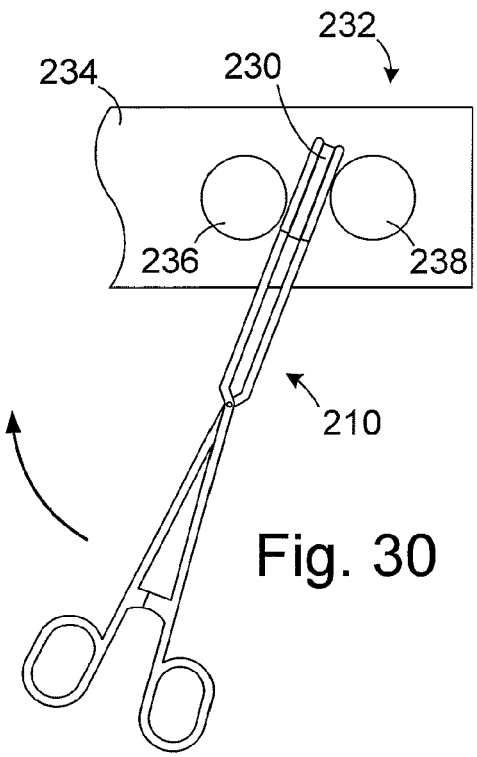
FIGS. 30 and 31 are plan views of the clamp illustrated in FIG. 27 being bent with the mandrel illustrated in FIG. 28.
Figure 31:
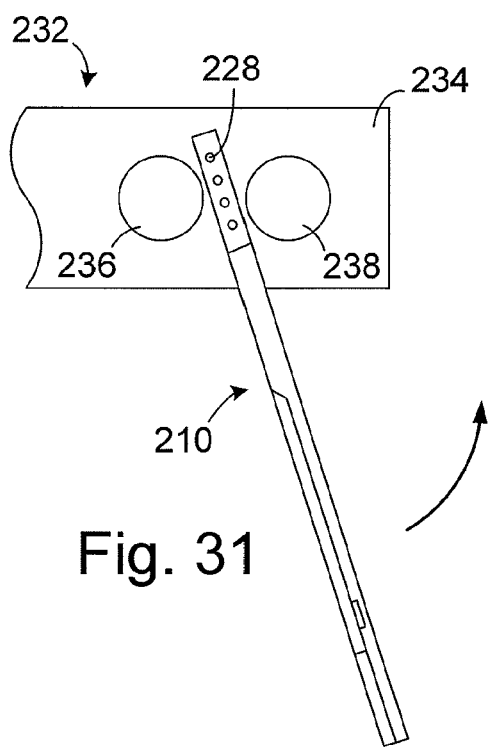
Figure 33:
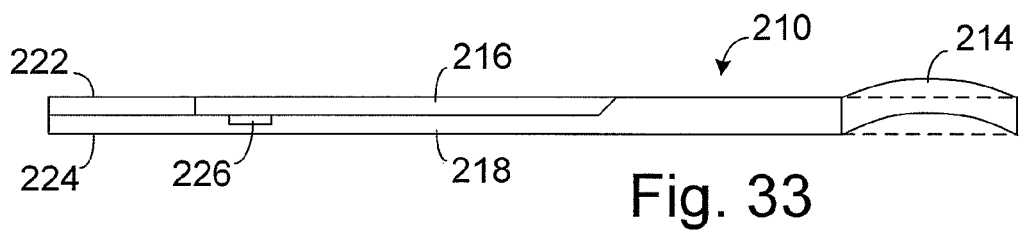
FIG. 33 is a plan view showing another example of how the clamp illustrated in FIG. 27 may be bent.

The exemplary mandrel 232 may be used to bend the malleable clamp members 212 and 214 in the manners illustrated in FIGS. 30 and 31. Referring first to FIG. 30, once the malleable clamp members 212 and 214 and malleable insert 230 have been placed between the posts 236 and 238, the clamp 210 may be rotated in the direction of the arrow (or in the opposite direction) until the damp members 212 and 214 are bent the desired amount. The damp 210 may then moved longitudinally and the bending process repeated until the desired bend, such as the exemplary bend illustrated in FIG. 32, has been achieved. Alternatively, or in addition, the clamp 210 can be rotated about its longitudinal axis and bent in other planes, as is illustrated for example in FIGS. 31 and 33. It should also be noted that, if desired, the malleable clamp members 212 and 214 may be bent independently of one another and/or into different shapes. Preferably, the physician will simply place the mandrel 232 on a suitable surface and press down the base 234 during a bending procedure. Alternatively, structure may be provided to secure the mandrel 232 to the surface.

Figure 34:
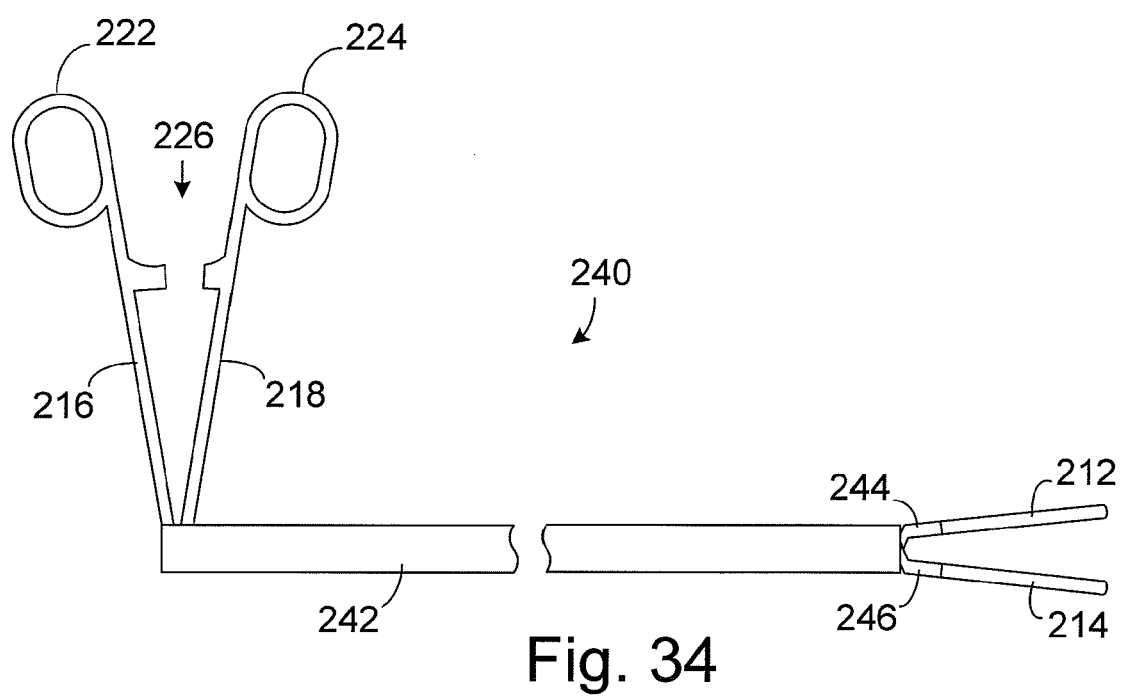
FIG. 34 is a plan view of a clamp in accordance with a preferred embodiment of a present invention.

Another example of a clamp in accordance with a preferred embodiment of a present invention is generally represented by reference numeral 240 in FIG. 34. Clamp 240 is similar to clamp 210 and similar elements are represented by similar reference numerals. The exemplary clamp 240 includes malleable clamp members 212 and 214, pivotable arms 216 and 218, handles 222 and 224, and a locking device 226. Here, however, the arms 216 and 218 are pivotably carried by one end of an elongate housing 242 and the malleable damp) members 212 and 214 are carried by a pair of supports 244 and 246 that are pivotably carried the other end of the housing. A suitable mechanical linkage (not shown) located within the housing 242 causes the supports 244 and 246 (and clamp members 212 and 214) to move relative to one another in response to movement of the arms 216 and 218. The housing 242 may be rigid or malleable The present clamps with malleable clamp members (such as exemplary damps 210 and 240) have a wide variety of applications. One example is the formation of transmural epicardial lesions to isolate the sources of focal (or ectopic) atrial fibrillation and, more specifically, the creation of transmural lesions around the pulmonary veins. Energy transmission devices may be permanently affixed to the malleable clamp members. Energy transmission devices may also be added using the structures described in Sections I-IV above and the clamp may be used a clamp or as a surgical probe, depending on the structure being used in combination with the clamp. Access to the heart may be obtained via a thoracotomy, thoracostomy or median sternotomy. Ports may also be provided for cameras and other instruments.

Lesions may be created around the pulmonary veins individually or, alternatively, lesions may be created around pairs of pulmonary veins. For example, a first transmural epicardial lesion may be created around the right pulmonary vein pair and a second transmural epicardial lesion may be created around the left pulmonary vein pair. Thereafter, if needed, a linear transmural epicardial lesion may be created between the right and left pulmonary vein pairs. A linear transmural lesion that extends from the lesion between the right and left pulmonary vein pairs to the left atrial appendage may also be formed. Alternatively, a single lesion may be formed around all four of the pulmonary veins.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

What is claimed is:

1. A tissue coagulation device for creating a lesion during a minimally invasive procedure, the device comprising:
   a clamp comprising a first clamp member and a second clamp member, the first and second clamp members coupled via a pivot; and
   an energy transmission assembly comprising an energy transmission device, a cable, and a base member having a slot that secures the energy transmission device, the base member having a proximal end and a distal end,
   wherein the base member is coupled with the first clamp member via a first mating structure and with the second clamp member via a second mating structure,
   wherein the base member is positioned between the first mating structure and the second mating structure,
   wherein the proximal end of the base is positioned distal to the pivot, and
   wherein the base member resists angular displacement between the first mating structure and the second mating structure.

2. The tissue coagulation device according to claim 1, wherein the first clamp member comprises a first clamp member slot, the second clamp member comprises a second clamp member slot, and the base member comprises the first mating structure and the second mating structure, and wherein the first mating structure and the second mating structure of the base member are sized and shaped to create a fit with the first clamp member slot and the second clamp member slot, respectively.

3. The tissue coagulation device according to claim 2, wherein the first mating structure and the second mating structures are disposed on opposing sides of the base member, and extend longitudinally therefrom.

4. The tissue coagulation device according to claim 1, wherein the first clamp member comprises the first mating structure, the second clamp member comprises the second mating structure, and the base member comprises a first slot and a second slot, and wherein the first clamp member mating structure and the second clamp member mating structure are sized and shaped to create a fit with the first slot and the second slot of the base member, respectively.

5. The tissue coagulation device according to claim 1, further comprising a wire and a temperature sensor, wherein the base member comprises a wire aperture, and wherein the wire is disposed within the wire aperture and the cable, is coupled with the temperature sensor, and is configured to transmit signals from the temperature sensor to an electrosurgical unit.

6. The tissue coagulation device according to claim 5, wherein the base member comprises a hole disposed between the wire aperture and the temperature sensor, and the wire runs through the hole.

7. The tissue coagulation device according to claim 1, further comprising a return energy transmission device, wherein the base member comprises a second slot that secures the return energy transmission device.

8. A tissue coagulation device for creating a lesion during a minimally invasive procedure, the device comprising:
   a clamp comprising a first clamp member and a second clamp member, the first and second clamp members coupled via a pivot; and
   an energy transmission assembly comprising an energy transmission device, a wire that conducts coagulation energy for emission by the energy transmission device, and a base member having a slot that secures the energy transmission device, the base member having a proximal end and a distal end,
   wherein the base member is coupled with the first clamp member via a first mating structure and with the second clamp member via a second mating structure,
   wherein the base member is positioned between the first mating structure and the second mating structure,
   wherein the proximal end of the base is positioned distal to the pivot, and
   wherein the base member resists angular displacement between the first mating structure and the second mating structure.

9. The tissue coagulation device according to claim 8, wherein the first clamp member comprises a first clamp slot, the second clamp member comprises a second clamp slot, and the base member comprises the first mating structure and the second mating structure, and wherein the first mating structure and the second mating structure of the base member are sized and shaped to create a fit with the first clamp member slot and the second clamp member slot, respectively.

10. The tissue coagulation device according to claim 9, wherein the first mating structure and the second mating structure are disposed on opposing sides of the base member, and extend longitudinally therefrom.

11. The tissue coagulation device according to claim 8, wherein the first clamp member comprises the first mating structure, the second clamp member comprises the second mating structure, and the base member comprises a first slot and a second slot, and wherein the first mating structure and the second mating structure are sized and shaped to create a fit with the first slot and the second slot of the base member, respectively.

12. The tissue coagulation device according to claim 8, further comprising a cable coupled with the base member, a temperature sensor wire, and a temperature sensor, wherein the base member comprises a wire aperture, and wherein the temperature sensor wire is disposed within the wire aperture and the cable, is coupled with the temperature sensor, and is configured to transmit signals from the temperature sensor to an electrosurgical unit.

13. The tissue coagulation device according to claim 12, wherein the base member comprises a holed disposed between the wire aperture and the temperature sensor, and the temperature sensor wire runs through the hole.

14. The tissue coagulation device according to claim 8, further comprising a return energy transmission device, wherein the base member comprises a second slot that secures the return energy transmission device.

\* \* \* \* \*